United States Patent
Wagner et al.

(10) Patent No.: US 9,913,976 B2
(45) Date of Patent: Mar. 13, 2018

(54) SYSTEMS AND METHODS FOR STIMULATING AND MONITORING BIOLOGICAL TISSUE

(75) Inventors: Timothy Andrew Wagner, Cambridge, MA (US); Uri Tzvi Eden, Somerville, MA (US)

(73) Assignee: Highland Instruments, Inc., Cambridge, MA (US)

( * ) Notice: Subject to any disclaimer, the term of this patent is extended or adjusted under 35 U.S.C. 154(b) by 963 days.

(21) Appl. No.: 13/162,047

(22) Filed: Jun. 16, 2011

(65) Prior Publication Data
US 2011/0275927 A1 Nov. 10, 2011

(51) Int. Cl.
| | |
|---|---|
| A61N 1/36 | (2006.01) |
| A61N 7/00 | (2006.01) |
| A61N 1/32 | (2006.01) |
| A61N 1/20 | (2006.01) |
| A61N 1/40 | (2006.01) |
| A61N 1/05 | (2006.01) |
| A61N 1/362 | (2006.01) |
| A61B 6/00 | (2006.01) |

(52) U.S. Cl.
CPC .............. *A61N 1/20* (2013.01); *A61N 1/32* (2013.01); *A61N 1/36017* (2013.01); *A61N 1/36182* (2013.01); *A61N 1/40* (2013.01); A61B 6/506 (2013.01); A61N 1/0529 (2013.01); A61N 1/362 (2013.01); A61N 1/36025 (2013.01); A61N 1/36071 (2013.01); A61N 1/36082 (2013.01); A61N 1/36096 (2013.01); A61N 1/36135 (2013.01); A61N 2007/0026 (2013.01)

(58) Field of Classification Search
CPC . A61N 7/00; A61N 1/205; A61N 1/36; A61N 1/326; A61N 1/327; A61N 1/325; A61N 2007/0026; A61N 1/36021; A61N 1/36025; A61B 2018/00994; A61F 7/00
USPC .................................................... 607/2–3, 45
See application file for complete search history.

(56) References Cited

U.S. PATENT DOCUMENTS

| | | | | |
|---|---|---|---|---|
| 2,830,578 | A | * | 4/1958 | Degroff ........................... 601/21 |
| 2,838,672 | A | | 6/1958 | Leah et al. |
| 3,735,756 | A | | 5/1973 | Richards et al. |

(Continued)

FOREIGN PATENT DOCUMENTS

| | | |
|---|---|---|
| WO | 2007/149811 A2 | 12/2007 |
| WO | 2010/009141 A1 | 1/2010 |

(Continued)

OTHER PUBLICATIONS

A. Priori "Brain Polarization in humans: a reappraisal of an old tool for prolonged non-invasive modulation of brain excitability", Clinical Neurophysiology 114 (2203) 589-595.*

(Continued)

*Primary Examiner* — Mark W Bockelman
(74) *Attorney, Agent, or Firm* — Brown Rudnick LLP

(57) ABSTRACT

The invention generally relates to apparatuses and methods for stimulating and monitoring biological tissue. In certain aspects, the invention provides a system for stimulating and monitoring tissue, the system including a first energy source, a second energy source, and an imaging device, in which the system is configured such that the first and second energy sources target the same region of tissue and the combined effect of the first and second energy sources stimulates the region of tissue.

17 Claims, 5 Drawing Sheets

(56) References Cited

U.S. PATENT DOCUMENTS

| | | |
|---|---|---|
| 3,822,708 A | 7/1974 | Zilber |
| 4,305,402 A | 12/1981 | Katims |
| 4,503,863 A | 3/1985 | Katims |
| 4,535,785 A | 8/1985 | van den Honert et al. |
| 4,611,596 A | 9/1986 | Wasserman |
| 4,641,633 A | 2/1987 | Delgado |
| 4,672,951 A | 6/1987 | Welch |
| 4,709,700 A | 12/1987 | Hyrman |
| 4,723,536 A | 2/1988 | Rauscher et al. |
| 4,759,377 A | 7/1988 | Dykstra |
| 4,805,636 A | 2/1989 | Barry et al. |
| 4,889,526 A | 12/1989 | Rauscher et al. |
| 4,923,437 A | 5/1990 | Gordon |
| 4,989,605 A | 2/1991 | Rossen |
| 5,014,699 A | 5/1991 | Pollack et al. |
| 5,061,234 A | 10/1991 | Chaney |
| 5,113,859 A | 5/1992 | Funke |
| 5,277,694 A | 1/1994 | Leysieffer et al. |
| 5,300,093 A | 4/1994 | Koestner et al. |
| 5,476,438 A | 12/1995 | Edrich et al. |
| 5,545,124 A | 8/1996 | Krause et al. |
| 5,551,953 A | 9/1996 | Lattin et al. |
| 5,569,591 A | 10/1996 | Kell et al. |
| 5,575,761 A | 11/1996 | Hajianpour |
| 5,582,586 A | 12/1996 | Tachibana et al. |
| 5,713,922 A | 2/1998 | King |
| 5,738,625 A | 4/1998 | Gluck |
| 5,776,170 A | 7/1998 | MacDonald et al. |
| 5,776,171 A | 7/1998 | Peckham et al. |
| 5,893,883 A | 4/1999 | Torgerson et al. |
| 5,895,416 A | 4/1999 | Barreras, Sr. et al. |
| 5,925,070 A | 7/1999 | King et al. |
| 5,975,085 A | 11/1999 | Rise |
| 6,021,348 A | 2/2000 | James |
| 6,035,236 A | 3/2000 | Jarding et al. |
| 6,066,084 A | 5/2000 | Edrich et al. |
| 6,066,163 A | 5/2000 | John |
| 6,081,744 A | 6/2000 | Loos |
| 6,091,992 A | 7/2000 | Bourgeois et al. |
| 6,094,598 A | 7/2000 | Elsberry et al. |
| 6,102,875 A | 8/2000 | Jones |
| 6,128,537 A | 10/2000 | Rise |
| 6,161,048 A | 12/2000 | Sluijter et al. |
| 6,169,403 B1 | 1/2001 | Hebrank et al. |
| 6,205,356 B1 | 3/2001 | Holcomb |
| 6,221,908 B1 | 4/2001 | Kilgard et al. |
| 6,231,527 B1 | 5/2001 | Sol |
| 6,231,604 B1 | 5/2001 | Von Ilberg |
| 6,234,953 B1 | 5/2001 | Thomas et al. |
| 6,275,735 B1 | 8/2001 | Jarding et al. |
| 6,275,737 B1 | 8/2001 | Mann |
| 6,330,476 B1 | 12/2001 | Ben-Haim et al. |
| 6,375,666 B1 | 4/2002 | Mische |
| 6,390,995 B1 | 5/2002 | Ogden et al. |
| 6,393,325 B1 | 5/2002 | Mann et al. |
| 6,408,211 B1 | 6/2002 | Powell |
| 6,432,070 B1 | 8/2002 | Talish et al. |
| 6,463,328 B1 | 10/2002 | John |
| 6,468,274 B1 | 10/2002 | Alleyne et al. |
| 6,491,039 B1 | 12/2002 | Dobak, III |
| 6,520,903 B1 | 2/2003 | Yamashiro |
| 6,520,911 B1 | 2/2003 | Wen |
| 6,535,767 B1 | 3/2003 | Kronberg |
| 6,536,440 B1 | 3/2003 | Dawson |
| 6,546,290 B1 | 4/2003 | Shloznikov |
| 6,567,702 B1 | 5/2003 | Nekhendzy et al. |
| 6,584,357 B1 | 6/2003 | Dawson |
| 6,591,138 B1 | 7/2003 | Fischell et al. |
| 6,615,080 B1 | 9/2003 | Unsworth et al. |
| 6,645,144 B1 | 11/2003 | Wen et al. |
| 6,654,642 B2 | 11/2003 | North et al. |
| 6,681,131 B2 | 1/2004 | Kandori et al. |
| 6,685,729 B2 | 2/2004 | Gonzalez |
| 6,692,490 B1 | 2/2004 | Edwards |
| 6,721,603 B2 | 4/2004 | Zabara et al. |
| 6,729,337 B2 | 5/2004 | Dawson |
| 6,764,498 B2 | 7/2004 | Mische |
| 6,824,515 B2 | 11/2004 | Suorsa et al. |
| 6,836,685 B1 | 12/2004 | Fitz |
| 6,858,000 B1 | 2/2005 | Schukin et al. |
| 6,866,678 B2 | 3/2005 | Shenderova et al. |
| 6,871,099 B1 | 3/2005 | Whitehurst et al. |
| 6,887,239 B2 | 5/2005 | Elstrom et al. |
| 6,889,085 B2 | 5/2005 | Dawson |
| 6,921,413 B2 | 7/2005 | Mahadevan-Jansen et al. |
| 6,934,580 B1 | 8/2005 | Osorio et al. |
| 6,937,906 B2 | 8/2005 | Terry et al. |
| 6,941,171 B2 | 9/2005 | Mann et al. |
| 6,964,643 B2 | 11/2005 | Hovland et al. |
| 6,970,744 B1 | 11/2005 | Shelchuk |
| 6,976,998 B2 | 12/2005 | Rizzo et al. |
| 7,002,790 B2 | 2/2006 | Hossick-Schott et al. |
| 7,003,352 B1 | 2/2006 | Whitehurst |
| 7,013,177 B1 | 3/2006 | Whitehurst et al. |
| 7,058,447 B2 | 6/2006 | Hill et al. |
| 7,104,947 B2 | 9/2006 | Riehl |
| 7,120,497 B2 | 10/2006 | Ben-Haim et al. |
| 7,146,210 B2 | 12/2006 | Palti |
| 7,173,130 B2 | 2/2007 | Tsien et al. |
| 7,283,861 B2 * | 10/2007 | Bystritsky ............... 600/411 |
| 7,894,903 B2 | 2/2011 | John |
| 8,197,409 B2 | 6/2012 | Foley et al. |
| 8,718,758 B2 | 5/2014 | Wagner et al. |
| 8,929,979 B2 | 1/2015 | Wagner et al. |
| 2001/0051774 A1 | 12/2001 | Littrup et al. |
| 2004/0131998 A1* | 7/2004 | Marom et al. ............... 434/236 |
| 2005/0043726 A1 | 2/2005 | McHale et al. |
| 2005/0043762 A1 | 2/2005 | Echt et al. |
| 2005/0075680 A1 | 4/2005 | Lowry et al. |
| 2006/0004422 A1 | 1/2006 | De Ridder |
| 2006/0017749 A1 | 1/2006 | McIntyre et al. |
| 2006/0247104 A1 | 11/2006 | Grabiner et al. |
| 2007/0043268 A1* | 2/2007 | Russell ............... A61B 6/501 600/300 |
| 2007/0060974 A1 | 3/2007 | Lozano |
| 2007/0156180 A1 | 7/2007 | Jaax et al. |
| 2007/0299370 A1 | 12/2007 | Bystritsky |
| 2008/0039895 A1 | 2/2008 | Fowler et al. |
| 2008/0046053 A1 | 2/2008 | Wagner et al. |
| 2008/0228110 A1 | 9/2008 | Berme |
| 2009/0018599 A1 | 1/2009 | Hastings et al. |
| 2009/0240170 A1 | 9/2009 | Rowley et al. |
| 2010/0268287 A1 | 10/2010 | Celnik |
| 2011/0275927 A1 | 11/2011 | Wagner et al. |
| 2012/0245653 A1* | 9/2012 | Bikson ............... A61N 1/36025 607/45 |

FOREIGN PATENT DOCUMENTS

| | | |
|---|---|---|
| WO | 2010/017392 A2 | 2/2010 |
| WO | 2012/101093 A2 | 8/2012 |
| WO | 2013/054257 A1 | 4/2013 |

OTHER PUBLICATIONS

W.J.Fry "Electrical Stimulation of Brain Localized without Probes—Theoretical Analysis of a propose Method", Journal of the Acoustical Society of America, vol. 44 No. 4 pp. 919-931, 1968.*

S.J. Norton "Can ultrasound be used to stimulate nerve tissue?" Biomedical Engineering OnLine 2003, 2:6.*

Gabriel, S., R.W. Lau, and C. Gabriel, The dielectric properties of biological tissues: II. Measurements in the frequency range 10 Hz to 20 GHz. Phys Med Biol, 1996. 41(11):2251-69.

Gabriel, S., R.W. Lau, and C. Gabriel, The dielectric properties of biological tissues: III. Parametric models for the dielectric spectrum of tissues. Phys Med Biol, 1996. 41(11):2271-93.

Gielen, F. Deep Brain Stimulation: Current Practice and Challenges for the Future. in 1st International IEEE EMBS Conference on Neural Engineering. 2003. Capri Island, Italy: IEEE.

Graziano, M.S., C.S. Taylor, and T. Moore, Complex movements evoked by microstimulation of precentral cortex. Neuron, 2002. 34(5):841-51.

(56) References Cited

OTHER PUBLICATIONS

Grill, W.M., et al., Temporal excitation properties of paresthesias evoked by thalamic microstimulation. Clin Neurophysiol, 2005. 116(5):1227-34.
Grill, W.M., S.E. Norman, and R.V. Bellamkonda, Implanted neural interfaces: biochallenges and engineered solutions. Annu Rev Biomed Eng, 2009. 11:1-24.
Grosse, C., Permitivity of suspension of charged particles in electolyte solution. J. Chem. Phys., 1987. 91:3073.
Gusev, V., et al., Imaging With the Ultrasonic Vibration Potential: A Theory for Current Generation. Ultrasound in Med. & Biol., 2005. vol. 31, No. 2:273-278.
Haar, G.t., Accoustic Surgery: Bursts of focused ultrasound energy three orders of magnitude more intense than diagnostic ultrasound are emerging as a noninvasive option for treating cancer and other medical procedures., Physics Today, 2001:29-34.
Hart FX, Toll RB, Berner NJ, Bennett NH, (1996), The low frequency dielectric properties of octopus arm muscle measured in vivo. Phys Med Biol 41:2043-2052.
Hart, F.X. and W.R. Dunfree, In vivo measurements of low frequency dielectric spectra of a frog skeletal muscle. Phys. Med. Biol., 1993, 38:1099-1112.
Hatanaka, N., et al., Input-output organization of jaw movement-related areas in monkey frontal cortex. J Comp Neural, 2005. 492(4):401-25.
Heller L, Hulsteyn DBv, (1992), Brain stimulation using electromagnetic sources: theoretical aspects. Biophysical Journal 63:129-138.
Hinch, E.J., et al., Dielectric response of a dilute suspension of spheres with thin double layers in an asymmetric electrolyte. J Chem Soc, Farady Tans., 1983. 80:535-551.
Holdefer, R.N., R. Sadleir, and M.J. Russell, Predicted current densities in the brain during transcranial electrical stimulation. Clin Neurophysiol, 2006. 117(6):1388-97.
Hole, S. and T. Ditchi, Non-destructive Methods for Space Charge Distribution Measurements: What are the Differences? IEEE EMBS, 2003. 10(4):670-677.
Hsiao, I. and V. Lin, Improved coil design for functional magnetic stimulation of expiratory muscles. IEEE Trans Biomed Eng, 2001. 48(6):684-694.
Hsu KH and D. DM., A 3-D differential coil design for localized magnetic stimulation. IEEE Trans Biomed Eng, 2001. 48(10):1162-8.
International Search Report for PCT/US2013/053006 dated Mar. 18, 2010 (3 pages).
Jones KE, Bawa P, (1997), Computer simulation of the responses of human motoneurons to composite 1A EPSPS: effects of background firing rate. J Neurophysiol 77:405-420.
Kanai, R., et al., Frequency-dependent electrical stimulation of the visual cortex. Curr Biol, 2008. 18(23):1839-43.
Kanner, A.M., Deep brain stimulation for intractable epilepsy: which target and for which seizures? Epilepsy Curr, 2004. 4(6):231-2.
Kaufman, E.F. and A.C. Rosenquist, Efferent projections of the thalamic intralaminar nuclei in the cat. Brain Res, 1985. 335(2):257-79.
Khachaturian, M.H., et al., Focal reversible deactivation of cerebral metabolism affects water diffusion. Magn Reson Med, 2008. 60(5):1178-89.
Khraiche, M.L., et al., Ultrasound induced increase in excitability of single neurons. Conf Proc IEEE Eng Med Biol Soc, 2008. 2008: p. 4246-9.
Kleim, J.A., T.A. Jones, and T. Schallert, Motor enrichment and the induction of plasticity before or after brain injury. Neurochem Res, 2003. 28(11):1757-69.
Komissarow, L., et al., Triple stimulation technique (TST) in amyotrophic lateral sclerosis. Clin Neurophysiol, 2004. 115(2):356-60.

Kraus, K.H., et al., The use of a cap-shaped coil for transcranial magnetic stimulation of the motor cortex. J Clin Neurophysiol, 1993. 10(3):353-62.
Kumar, K., C. Toth, and R.K. Nath, Deep brain stimulation for intractable pain: a 15-year experience. Neurosurgery, 1997. 40(4):736-46; Discussion 746-7.
Larkin, J., et al., Combined electric field and ultrasound therapy as a novel anti-tumour treatment. European Journal of Cancer 41 (2005):1339-1348.
Lemay, M.A., et al., Endpoint forces obtained during intraspinal microstimulation of the cat lumbar spinal cord—experimental and biomechanical model results. In IEEE 28th Annual Northeast Bioengineering Conference, 2002, IEEE.
Li, D.L., et al. Finite element analysis of transcranial electrical stimulation for intraoperative monitoring. in Bioengineeng Conference, Proceedings of the IEEE 31st Annual Northeast 2005, IEEE.
Lin, V., I. Hsiao, and V. Dhaka, Magnetic coil design considerations for functional magnetic stimulation. IEEE Trans Biomed Eng, 2000. 47(5):600-610.
Lomber, S.G., The advantages and limitations of permanent or reversible deactivation techniques in the assessment of neural function. J Neurosci Methods, 1999. 86(2):109-17.
Lozano, A.M., et al., Deep brain stimulation for Parkinson's disease: disrupting the disruption. Lancet Neurol, 2002. 1(4):225-31.
Luber, B., et al., Remediation of sleep-deprivation-induced working memory impairment with fMRI-guided transcranial magnetic stimulation. Cereb Cortex, 2008. 18(9):2077-85.
McCreery D, Agnew W, (1990), Neuronal and axonal injury during functional electrical stimulation; a review of the possible mechanisms. In: Annual International Conference of the IEEE Engineering in Medicine and Biology Society, p. 1489:IEEE.
McCreery, D., et al., Accessing the Tonotopic Organization of the Ventral Cochlear Nucleus by Intranuclear Microstimulation. IEEE Trans Rehabil Eng, 1998. 6(4):391-399.
McCreery, D., et al., Charge Density and Charge Per Phase as Cofactors in Neural Injury Induced by Electrical Stimulation. IEEE Trans Biomed Eng, 1990. 37(10):996-1001.
McIntyre, C.C. and W.M. Grill, Excitation of central nervous system neurons by nonuniform electric fields, Biophys J, 1999. 76(2):878-88.
McIntyre, C.C. and W.M. Grill, Extracellular stimulation of central neurons: influence of stimulus waveform and frequency on neuronal output. J Neurophysiol, 2002. 88(4):1592-604.
McIntyre, C.C., et al., Cellular effects of deep brain stimulation: model-based analysis of activation and inhibition. J Neurophysiol, 2004. 91(4):1457-69.
McIntyre, C.C., et al., Electric field and stimulating influence generated by deep brain stimulation of the subthalamic nucleus. Clin Neurophysiol, 2004. 115(3):589-95.
McNeal DR, (1976), Analysis of a model for excitation of myelinated nerve. IEEE Trans Biomed Eng 23:329-337.
McRee, D.I. and H. Wachtel, Elimination of microwave effects on the vitality of nerves after blockage of active transport Radiat Res, 1986. 108(3):260-8.
McRee, D.I. and H. Wachtel, Pulse microwave effects on nerve vitality. Radiat Res, 1982. 91(1):212-8.
McRee, D.I. and H. Wachtel, The effects of microwave radiation on the vitality of isolated frog sciatic nerves. Radiat Res, 1980. 82(3):536-46.
Medtronic, Active® PC Implant Manual, Medtronic, Editor. 2007, Medtronic: Minneapolis.
Mihran, R.T., et al., Temporally-Specific Modification of Myelinated Axon Excitability in Vitro Following a Single Ultrasound Pulse. Ultrasound in Med. & Biol., 1990, vol. 16, No. 3:297-309.
Miocinovic, S. and W.M. Grill, Sensitivity of temporal excitation properties to the neuronal element activated by extracellular stimulation. J Neurosci Methods, 2004. 132(1):91-9.
Miranda, P.C., M. Hallett, and P.J. Basser, The electric field induced in the brain by magnetic stimulation: a 3-D finite-element analysis of the effect of tissue heterogeneity and anisotropy. IEEE Trans Biomed Eng, 2003. 50(9):1074-85.

(56) References Cited

OTHER PUBLICATIONS

Miranda, P.C., M. Lomarev, and M. Hallett, Modeling the current distribution during transcranial direct current stimulation. Clin Neurophysiol, 2006. 117(7):1623-9.
Montalibet, A., et al., Electric current generated by ultrasonically induced Lorentz force in biological media. Med. Biol. Eng. Comput., 2001, vol. 39:15-20.
Mouchawar, G., et al., Magnetic Stimulation of excitable tissue: calculation of induced eddy currents with a three-dimensional finite-element model. IEEE Transactions on Magnetics, 1993. 29(6):3355-3357.
Murasugi, C.M., C.D. Salzman, and W.T. Newsome, Microstimulation in visual area MT: effects of varying pulse amplitude and frequency. J Neurosci, 1993. 13(4):1719-29.
Mushahwar, V.K. and K.W. Horch, Selective activation of muscle groups in the feline hindlimb through electrical microstimulation of the ventral lumbo-sacral spinal cord. IEEE Trans Rehabil Eng, 2000. 8(1):11-21.
Nadeem, M., et al., Computation of electric and magnetic stimulation in human head using the 3-D impedance method. IEEE Transactions on Biomedical Engineering, 2003. 50(7):900-907.
Nagarajan, S. and D.M. Durand, Analysis of magnetic stimulation of a concentric axon in a nerve bundle. IEEE Transactions on Biomedical Engineering, 1995. 42(9):926-933.
Nagarajan, S., D.M. Durand, and E.N. Warman, Effects of induced electric fields on finite neuronal structures: a simulation study. IEEE Transactions on Biomedical Engineering, 1993. 40(11):1175-1188.
Nagarajan, S., et al. Magnetic stimulation of finite neuronal structures. in Annual International Conference of the IEEE Engineering in Medicine and Biology Society. 1991: IEEE.
Nathan, S.S., et al., Determination of current density distributions generated by electrical stimulation of the human cerebral cortex. Electroencephalogr Clin Neurophysiol, 1993. 86(3):183-92.
Neri Accornero et al., 'Visual evoked potentials modulation during direct current cortical polarization', Experimental Brain Research, Oct. 19, 2006, vol. 178, No. 2, pp. 261-286.
Nichols, M.J. and W.T. Newsome, Middle temporal visual area microstimulation influences veridical judgments of motion direction. J Neurosci, 2002. 22(21):9530-40.
Northstar Neuorsciences, Northstar Neuroscience Announces Primary Endpoint Results of Everest Clinical Trial. 2008: Seattle, (Downloaded from the Internet May 25, 2013).
Norton, 2003, Can ultrasound be used to stimulate nerve tissue, BioMedical Engineering OnLine 2(6):1-9.
O'Brien, W.D., Jr., Ultrasound-biophysics mechanisms. Prog Biophys Mol Biol, 2007. 93(1-3):212-55.
Pascual-Leone, A., D. Bartres-Faz, and J.P. Keenan, Transcranial magnetic stimulation: studying the brain-behaviour relationship by induction of 'virtual lesions'. Philos Trans R Soc Lond B Biol Sci, 1999. 354(1387):1229-38.
Perlmutter, J.S. and J.W. Mink, Deep Brain Stimulation. Annu Rev Neurosci, 2006:229-257.
Pernot, M., et al., In vivo transcranial brain surgery with an ultrasonic time reversal mirror. J Neurosurg, 2007. 106(6):1061-6.
Plonsey R, Heppner DB, (1967), Considerations of quasi-stationarity in electrophysiological systems. Bull Math Biophys 29:657-664.
Priori, A., Brain polarization in humans: a reappraisal of an old tool for prolonged non-invasive modulation of brain excitability. Clin Neurophysiol, 2003. 114(4):589-95.
Prochazka, A., V.K. Mushahwar, and D.B. McCreery, Neural prostheses. J Physiol, 2001. 533(Pt 1):99-109.
Purpura, D.P. and J.G. McMurtry, Intracellular Activities and Evoked Potential Changes During Polarization of Motor Cortex. J Neurophysiol, 1965. 28:166-85.
Ramos-Estebanez, C., et al., Visual phosphene perception modulated by subthreshold crossmodal sensory stimulation J Neurosci, 2007. 27(15):4178-81.
Ranck, J.B., Jr., Which elements are excited in electrical stimulation of mammalian central nervous system: a review. Brain Res, 1975. 98(3):417-40.

Rattay, F., et al., Mechanisms of Electrical Stimulation with Neural Prostheses. Neuromodulation, 2003. 6(1):42-56.
Rezai, A.R., et al., Deep brain stimulation for Parkinson's disease: surgical issues. Mov Disord, 2006. 21 Suppl 14:S197-218.
Romo, R., et al., Somatosensory discrimination based on cortical microstimulation. Nature, 1998. 392(6674):387-90.
Roth, B.J., Mechanisms for electrical stimulation of excitable tissue. Critical Reviews in Biomedical Engineering, 1994. 22(3-4):253-305.
Rousche, P. and R. Normann, Chronic Intracortical Microstimulation (ICMS) of Cat Sensory Cortex Using the Utah Intracortical Electrode Array. IEEE Trans Rehabil Eng, 1999. 7(1):56-68.
Rush, S. and D.A. Driscoll, Current distribution in the brain from surface electrodes. Anesth Analg, 1968. 47(6):717-23.
Rutten, W.L.C., et al., The influence of ultrasound and ultrasonic focusing on magnetic and electric peripheral nerve stimulation., in Advances in Magnetic Stimulation: Mathematical modeling and clinical applications, J. Nilsson, M. Panizza, and F. Grandori, Editors. 1996: Pavia, Italy, (p. 152).
Salzman, C.D., et al., Microstimulation in visual area MT: effects on direction discrimination performance. J Neurosci, 1992. 12(6):2331-55.
Salzman, C.D., K.H. Britten, and W.T. Newsome, Cortical microstimulation influences perceptual judgements of motion direction. Nature, 1990. 346(6280):174-7.
Saypol, J.M., et al., A theoretical comparison of electric and magnetic stimulation of the brain. Annals of Biomedical Engineering, 1991. 19(3):317-28.
Schmidt, E.M., et al., Feasibility of a visual prosthesis for the blind based on intracortical microstimulation of the visual cortex. Brain, 1996. 119 ( Pt 2):507-22.
Schwartzbaum, J.S., Electrophysiology of taste, feeding and reward in lateral hypothalamus of rabbit. Physiol Behav, 1988. 44(4-5):507-26.
Schwarz, G.J., A Theory of the Low Fequency Dielectric Dispersion of Colloidal Particles in Electrolyte Solutions, J Phys Chem, 1962. 66:2636.
Scivill, I., A.T. Barker, and I.L. Freeston, Finite element modelling of magnetic stimulation of the spine. Proceedings 18th annual international conference of the IEEE engineering in medicine and biology society, 1996:393-394.
Seidemann, E. and W.T. Newsome, Effect of spatial attention on the responses of area MT neurons. J Neurophysiol, 1999. 81(4):1783-94.
Seidemann, E., et al., Color signals in area MT of the macaque monkey. Neuron, 1999. 24(4):911-7.
Shupak, N.M., et al., Exposure to a specific pulsed low-frequency magnetic field: a double-blind placebo-controlled study of effects on pain ratings in rheumatoid arthritis and fibromyalgia patients. Pain Res Manag, 2006. 11(2):85-90.
Spiegel, R.J., et al., Measurement of small mechanical vibrations of brain tissue exposed to extremely-low-frequency electric fields. Bioelectromagnetics, 1986. 7(3):295-306.
Stecker, M.M., T. Patterson, and B.L. Netherton, Mechanisms of electrode induced injury. Part 1: theory. Am J Electroneurodiagnostic Technol, 2006. 46(4):315-42.
Stojanovic, M.P. and S. Abdi, Spinal cord stimulation. Pain Physician, 2002. 5(2):156-66.
Stoney, S.D., Jr., W.D. Thompson, and H. Asanuma, Excitation of pyramidal tract cells by intracortical microstimulation: effective extent of stimulating current. J Neurophysiol, 1968. 31(5):659-69.
Tehovnik, E.J. and W.M. Slocum, Microstimulation of V1 affects the detection of visual targets: manipulation of target contrast. Exp Brain Res, 2005. 165(3):305-14.
Tehovnik, E.J., Electrical stimulation of neural tissue to evoke behavioral responses. J Neurosci Methods, 1996. 65(1):1-17.
Terzuolo, C.A. and T.H. Bullock, Measurment of Imposed Voltage Gradient Adequate to Modulate Neuronal Firing. Proc Nati Acad Sci U S A, 1956. 42(9):687-694.
Thickbroom, G.W., Transcranial magnetic stimulation and synaptic plasticity: experimental framework and human models. Exp Brain Res, 2007. 180(4):583-93.

(56) References Cited

OTHER PUBLICATIONS

Thomas, A.W., D.J. Drost, and F.S. Prato, Human subjects exposed to a specific pulsed (200 microT) magnetic field: effects on normal standing balance. Neurosci Lett, 2001. 297(2):121-4.
Tofts, P.S., The distribution of induced currents in magnetic stimulation of the nervous system. Physical Medicine and Biology, 1990. 35:1119-1128.
Tranchina, D. and C. Nicholson, A model for the polarization of neurons by extrinsically applied electric fields. Biophys J, 1986. 50(6):1139-56.
Traub RD, (1977), Motorneurons of different geometry and the size principle. Biol Cybern 25:163-176.
Troster, A.I., et al., Neuropsychological deficits in essential tremor: an expression of cerebello-thalamo-cortical pathophysiology? Eur J Neural, 2002. 9(2):143-51.
Tyler, W.J., et al., Remote excitation of neuronal circuits using low-intensity, low-frequency ultrasound. PLoS One, 2008. 3(10):e3511.
Ueno, S., T. Tashiro, and K. Harada, Localised stimulation of neural tissues in the brain by means of a paired configuration of time-varying magnetic fields. J. Appl. Phys., 1988. 64:5862-5864.
Wagner T, Valero-Cabre A, Pascual-Leone A, (2007), Noninvasive Human Brain Stimulation. Annu Rev Biomed Eng., 7.1:19.1-19.39.
Wagner TA, Zahn M, Grodzinsky AJ, Pascual-Leone A, (2004), Three-dimensional head model simulation of transcranial magnetic stimulation. IEEE Trans Biomed Eng 51:1586-1598.
Wagner, T., et al., Biophysical foundations underlying TMS: Setting the stage for an effective use of neurostimulation in the cognitive neurosciences. Cortex 45, 2008:1025-1034.
Wagner, T., et al., Transcranial direct current stimulation: a computer-based human model study. Neuroimage, 2007. 35(3):1113-24.
Wagner, T., et al., Transcranial magnetic stimulation and brain atrophy: a computer-based human brain model study. Exp Brain Res 189, 2008:539-550.
Wagner, T., et al., Transcranial magnetic stimulation and stroke: a computer-based human model study. Neuroimage, 2006. 30(3):857-70.
Wagner, T., Field distributions within the human cortex induced by transcranial magnetic stimulation, in EECS. 2001, Massachusetts Institute of Technology: Cambridge., Chapters 1 and 2, (126 pages).
Warman, E.N., W.M. Grill, and D. Durand, Modeling the effects of electric fields on nerve fibers: determination of excitation thresholds. IEEE Trans Biomed Eng, 1992. 39(12):1244-54.
Wichmann, T. and M.R. Delong, Deep brain stimulation for neurologic and neuropsychiatric disorders. Neuron, 2006. 52(1):197-204.
Wininger, F.A., J.L. Schei, and D.M. Rector, Complete optical neurophysiology: toward optical stimulation and recording of neural tissue. Appl Opt, 2009. 48(10):D218-24.
Wobschall, D., Bilayer Membrane Elasticity and Dynamic Response. Journal of Colloid and Interface Science, 1971. 36(3):385-396.
Wobschall, D., Voltage Dependence of Bilayer Membrane Capacitance. Journal of Colloid and Interface Science, 1972 40(3):417-423.
Wongsampigoon, A. and W.M. Grill, Computational modeling of epidural cortical stimulation. J Neural Eng, 2008. 5(4):443-54.
Zangen, A., et al., Transcranial magnetic stimulation of deep brain regions: evidence for efficacy of the H-coil. Clin Neurophysiol, 2005. 116(4):775-9.
Advanced Development for Defense Science and Technology, Apr. 5, 2010, 93 pages.
Allen, E.A., et al., Transcranial magnetic stimulation elicits coupled neural and hemodynamic consequences. Science, 2007. 317(5846): p. 1918-21.
Aydin-Abidin, S., et al., Effects of repetitive TMS on visually evoked potentials and EEG in the anesthetized cat: dependence on stimulus frequency and train duration. J Physiol, 2006:443-455.
Benabid, A.L., et al., Deep brain stimulation of the corpus luysi (subthalamic nucleus) and other targets in Parkinson's disease. Extension to new indications such as dystonia and epilepsy. J Neurol, 2001. 248 Suppl 3: p. III37-47.
Bindman LJ, L.O., Redfearn JW., Long-lasting changes in the level of the electrical activity of the cerebral cortex produced by polarizing currents. Nature 1962. 196:584-85.
Bindman, L.J., O.C. Lippold, and J.W. Redfearn, The Action of Brief Polarizing Currents on the Cerebral Cortex of the Rat (1) During Current Flow and (2) in the Production of Long-Lasting after-Effects. J Physiol, 1964. 172:369-82.
Bostock, H., The strength-duration relationship for excitation of myelinated nerve: computed dependence on membrane parameters. J Physiol, 1983. 341: p. 59-74.
Boyden, E.S., et al., Millisecond-timescale, genetically targeted optical control of neural activity. Nat Neurosci, 2005. 8(9):1263-8.
Brice, J. and L. McLellan, Suppression of intention tremor by contingent deep-brain stimulation. Lancet, 1980. 1(8180):1221-2.
Britten, K.H. and R.J. van Wezel, Electrical microstimulation of cortical area MST biases heading perception in monkeys. Nat Neurosci, 1998. 1(1):59-63.
Brown, J.A., et al., Motor cortex stimulation for the enhancement of recovery from stroke: a prospective, multicenter safety study. Neurosurgery, 2006. 58(3): p. 464-73.
Butovas, S. and C. Schwarz, Spatiotemporal effects of microstimulation in rat neocortex: a parametric study using multielectrode recordings. J Neurophysiol, 2003. 90(5):3024-39.
Butson CR, McIntyre CC (2005) Tissue and electrode capacitance reduce neural activation volume during deep brain stimulation. Clin Neurophysiol 116:2490-2500.
Butson, C.R. and C.C. McIntyre, Role of electrode design on the volume of tissue activated during deep brain stimulation. J Neural Eng, 2006. 3(1): p. 1-8.
Butson, C.R. and C.C. McIntyre. Deep brain Stimulation of the the subthalamic nucleus: model-based analysis of the effects of electrode capacitance on the volume of activation. in 2nd International IEEE EMBS Conference on Neural Engineerin. 2005. Arlington, VA: IEEE.
Carbunaru, R. and D.M. Durand, Toroidal coil models for transcutaneous magnetic stimulation of nerves. IEEE Trans Biomed Eng, 2001. 48(4):434-41.
Chew, W.C. and P.N. Sen, Dielectric enhancement due to an electrochemical double layer: thin double layer approximation. J. Chem. Phys., 1982. 77:4683.
Chew, W.C., 1983, Dielectric enhancement and electrophoresis due to electrochmical double layer: A uniform approximation. J Chem Phys. 80(9):4541-4552.
Clement, G.T. and K. Hynynen, A non-invasive method for focusing ultrasound through the human skull. Phys Med Biol, 2002. 47(8):1219-36.
Clement, G.T., et al., A magnetic resonance imaging-compatible, large-scale array for trans-skull ultrasound surgery and therapy. J Ultrasound Med, 2005. 24(8):1117-25.
Clement, G.T., Perspectives in clinical uses of high-intensity focused ultrasound. Ultrasonics, 2004. 42(10):1087-93.
Cohen, D. and B.N. Cuffin, Developing a more focal magnetic stimulator. Part 1: some basic principles. Journal of Clinical Neurophysiology, 1991. 8:102-111.
Cohen, L.G., et al., Effects of coil design on delivery of focal magnetic stimulation. Technical considerations. Electroencephalogr Clin Neurophysiol, 1990. 75(4):350-7.
Cohen, M.R. and W.T. Newsome, What electrical microstimulation has revealed about the neural basis of cognition. Curr Opin Neurobiol, 2004. 14(2):169-77.
Connor, C.W. and K. Hynynen, Patterns of Thermal Deposition in the Skull During Transcranial Focused Ultrasound Surgery. IEEE Trans Biomed Eng, 2004. 51(10):1693-1706.
Connor, C.W., G.T. Clement, and K. Hynynen, A unified model for the speed of sound in cranial bone based on genetic algorithm optimization. Phys Med Biol, 2002. 47(22):3925-44.
Cramer, S.C., et al., Use of functional MRI to guide decisions in a clinical stroke trial. Stroke, 2005. 36(5):e50-2.
Deuschl, G., et al., Deep brain stimulation: postoperative issues. Mov Disord, 2006. 21 Suppl 14:S219-37.

(56) References Cited

OTHER PUBLICATIONS

Di Lazzaro, V., et al., The physiological basis of transcranial motor cortex stimulation in conscious humans. Clin Neurophysiol, 2004. 115(2):255-66.
Diamond, A. and J. Jankovic, The effect of deep brain stimulation on quality of life in movement disorders. J Neurol Neurosurg Psychiatry, 2005. 76(9):1188-93.
Diokno, A.C., P.B. Leu, and D.B. Konstandt, A simplified method of implanting a neuromodulator device. J Urol, 2003. 169(4):1466-9.
Dissado, L.A., A fractal interpertation of the dielectric response of animal tissues. Phys. Med. Biol., 1990. 35(11):1487-1503.
Ditterich, J., M.E. Mazurek, and M.N. Shadlen, Microstimulation of visual cortex affects the speed of perceptual decisions. Nat Neurosci, 2003. 6(8):891-8.
Donald I. McRee, Howard Wachtel, Pulse Microwave Effects on Nerve Vitality, Radiation Research, vol. 91, No. 1, (1982):212-218.
Duck, F.A., Medical and non-medical protection standards for ultrasound and infrasound. Prog Biophys Mol Biol, 2007. 93(1-3):176-91.
Durand, D. and M. Bikson, Suppression and control of epileptiform activity by electrical stimulation: a review. Proceedings of the IEEE, 2001. 89(7):1065-1082.
Eaton, H., Electric field induced in a spherical volume conductor from arbitrary coils: applications to magnetic stimulation and MEG. Medic Biol Eng Comput, 1992:433-440.
Esselle, K. and M. Stuchly, Neural stimulation with magnetic fields: analysis of induced electrical fields. IEEE Transactions on Biomedical Engineering, 1992. 39:693-700.

Extended European Search Report for Application No. 12826175.7 dated Mar. 9, 2015 (6 pages).
Extended Supplementary European Search Report for Application No. Patent No. 12752660.6 dated Jul. 9, 2014 (6 pages).
Fields, J.A., et al., Neuropsychological and quality of life outcomes 12 months after unilateral thalamic stimulation for essential tremor. J Neural Neurosurg Psychiatry, 2003. 74(3):305-11.
Fixman, M., Charged macromolecules in external fields. I. The sphere. J Chem Phys, 1980. 72(9):5177-5186.
Fixman, M., Thin double layer approximation for electrophoresis and dielectric respons. J Chem Phys, 1982. 78(3):1483-1492.
FralexTherapeutics, Fralex Provides Update on Relief Trial. 2008: Toronto, (Downloaded from the Internet May 25, 2013).
Fregni, F. and A. Pascual-Leone, Technology insight: noninvasive brain stimulation in neurology-perspectives on the therapeutic potential of rTMS and tDCS. Nat Clin Pract Neurol, 2007. 3(7):383-93.
Fry WJ, W.V., Tucker D, Fry FJ, Physical factors involved in ultrasonically induced changes in living systems: I. Identification of non-temperature effects. J Acoust Soc Am 1950. 22:867-876.
Fry, E.J., An ultrasonic projector design for a wide range of research applications. Rev Sci Instrum, 1950. 21(11):940-1.
Fry, W. J., Electrical Stimulation of Brain Localized Without Probes—Theoretical Analysis of a Proposed Method, J Acoust Soc AM 44(4):919-31 (1968).
Fry, W.J., Use of intense ultrasound in neurological research. Am J Phys Med, 1958. 37(3):143-7.
Gabriel, C., S. Gabriel, and E. Corthout, The dielectric properties of biological tissues: I. Literature survey. Phys Med Biol, 1996. 41(11):2231-49.

\* cited by examiner

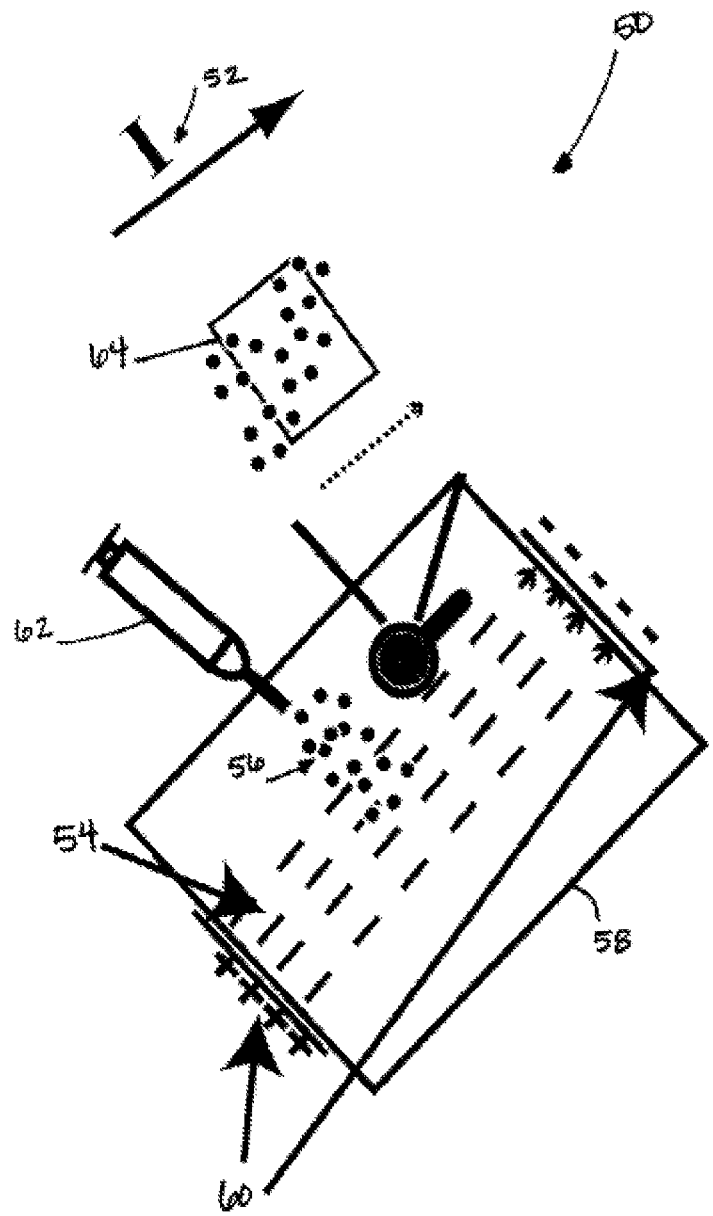

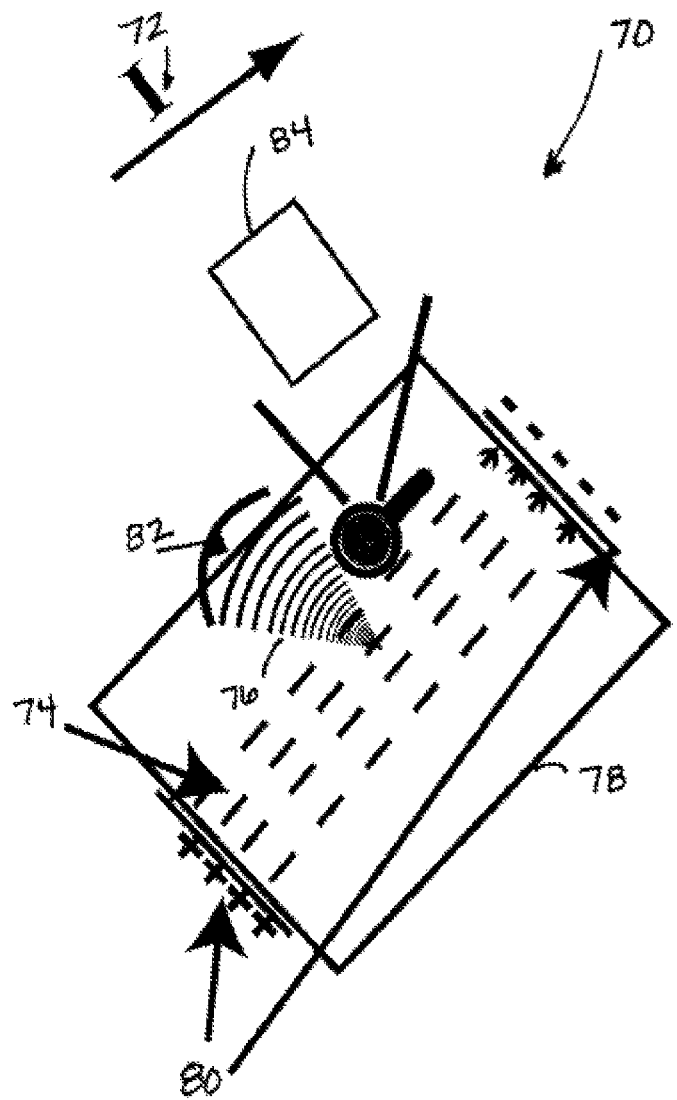

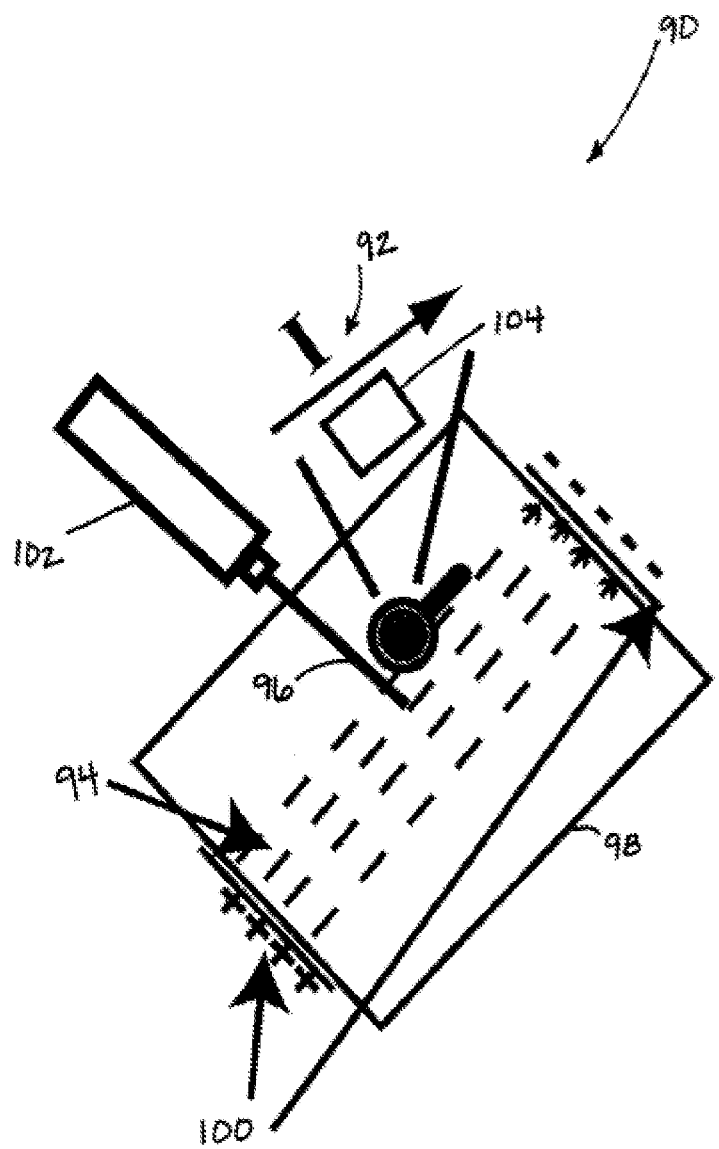

SYSTEMS AND METHODS FOR STIMULATING AND MONITORING BIOLOGICAL TISSUE

RELATED APPLICATIONS

The present application is a continuation-in-part of U.S. nonprovisional application Ser. No. 11/764,468, filed Jun. 18, 2007, which claims the benefit of and priority to U.S. provisional application Ser. No. 60/814,843, filed Jun. 19, 2006, the content of each of which is incorporated by reference herein in its entirety.

FIELD OF THE INVENTION

The invention generally relates to systems and methods for stimulating and monitoring biological tissue.

BACKGROUND

Stimulation of tissue in humans and other animals is used in a number of clinical applications as well as in clinical and general biological research. In particular, stimulation of neural tissue has been used in the treatment of various diseases including Parkinson's disease, depression, and intractable pain. The stimulation may be applied invasively, e.g., by performing surgery to remove a portion of the skull and implanting electrodes in a specific location within brain tissue, or non-invasively, e.g., transcranial direct current stimulation and transcranial magnetic stimulation.

A problem with tissue stimulation is an inability to monitor an effect of the stimulation on the tissue, particularly in real-time. For example, non-invasive stimulation of brain tissue involves stimulation of a large area of tissue that is generally not well characterized and that can be significantly perturbed by natural or pathological features of the brain tissue. The lack of monitoring makes it difficult to effectively target (localize) the stimulation to the desired region of tissue, dose the stimulation, and characterize safety parameters.

SUMMARY

The invention provides systems and methods that integrate tissue stimulation with monitoring of at least the stimulated tissue. Systems and methods of the invention allow for implementation of a closed loop system that allows for tuning of stimulation based on real-time feedback that is gathered from a monitoring device, e.g., an imaging device. In this manner, the stimulation can be modified to achieve a desired response relative to the information/feedback that is gathered. Particularly, data generated from real-time monitoring of the tissue that is stimulated can be used to modulate the stimulation by aiding in the targeting (localizing) of stimulation, dosing of stimulation, characterizing safety parameters, analyzing the online and/or effects of stimulation, and/or maximizing the therapeutic effect of stimulation.

In certain aspects, the invention provides systems for stimulating and monitoring tissue. In certain embodiments, the systems include a first energy source, a second energy source, and an imaging device, in which the system is configured such that the first and second energy sources target the same region of tissue and the combined effect of the first and second energy sources stimulates the region of tissue. Any imaging device known in the art may be used with systems of the invention. Exemplary imaging devices include a magnetic resonance imaging device, a functional magnetic resonance imaging device, a device for performing a CT scan, and a device for performing electroencephalography. In certain embodiments, the imaging device provides feedback to an operator as to the effect of the first and second energy sources on the tissue.

Any energy sources known in the art may be used with systems of the invention. In certain embodiments, the first energy source is an electric source that produces an electric field. The electric filed may be pulsed, time varying, pulsed a plurality of time with each pulse being for a different length of time, or time invariant. In certain embodiments, the second energy source is a source that produces a mechanical field, such as an ultrasound device. The mechanical filed may be pulsed, time varying, or pulsed a plurality of time with each pulse being for a different length of time. In certain embodiments, the electric field and/or the mechanical field is focused.

The first and second energy sources may be applied to any tissue. In certain embodiments, the first and second energy sources are applied to a structure or multiple structures within the brain or the nervous system such as the dorsal lateral prefrontal cortex, any component of the basal ganglia, nucleus accumbens, gastric nuclei, brainstem, thalamus, inferior colliculus, superior colliculus, periaqueductal gray, primary motor cortex, supplementary motor cortex, occipital lobe, Brodmann areas 1-48, primary sensory cortex, primary visual cortex, primary auditory cortex, amygdala, hippocampus, cochlea, cranial nerves, cerebellum, frontal lobe, occipital lobe, temporal lobe, parietal lobe, sub-cortical structures, and spinal cord. In particular embodiments, the tissue is neural tissue, and the affect of the stimulation alters neural function past the duration of stimulation.

Another aspect of the invention provides methods for stimulating and monitoring tissue. In certain embodiments, methods of the invention involve applying a first type of energy to a region of tissue, applying a second type of energy to the region of tissue, the combined effect of the first and second energy sources stimulates the region of tissue, and imaging at least the region of tissue. The imaging may provide feedback as to the effect of the first and second types of energy provided to the tissue. In certain embodiments, applying and imaging occur simultaneously. In other embodiments, applying and imaging occur sequentially.

BRIEF DESCRIPTION OF THE DRAWINGS

The above-mentioned and other features and objects of this invention, and the manner of attaining them, will become more apparent and the invention itself will be better understood by reference to the following description of embodiments of the invention taken in conjunction with the accompanying drawings, wherein:

FIG. 3 is a top plan view of an exemplary embodiment of an apparatus for stimulating biological tissue implementing a chemical source for altering permittivity constructed in accordance with the principles of the present disclosure;

FIG. 4 is a top plan view of an exemplary embodiment of an apparatus for stimulating biological tissue implementing a radiation source for altering permittivity constructed in accordance with the principles of the present disclosure; and FIG. 5 is a top plan view of another exemplary embodiment of an apparatus for stimulating biological tissue implementing an optical beam for altering permittivity constructed in accordance with the principles of the present disclosure.

DETAILED DESCRIPTION

Figure 1:
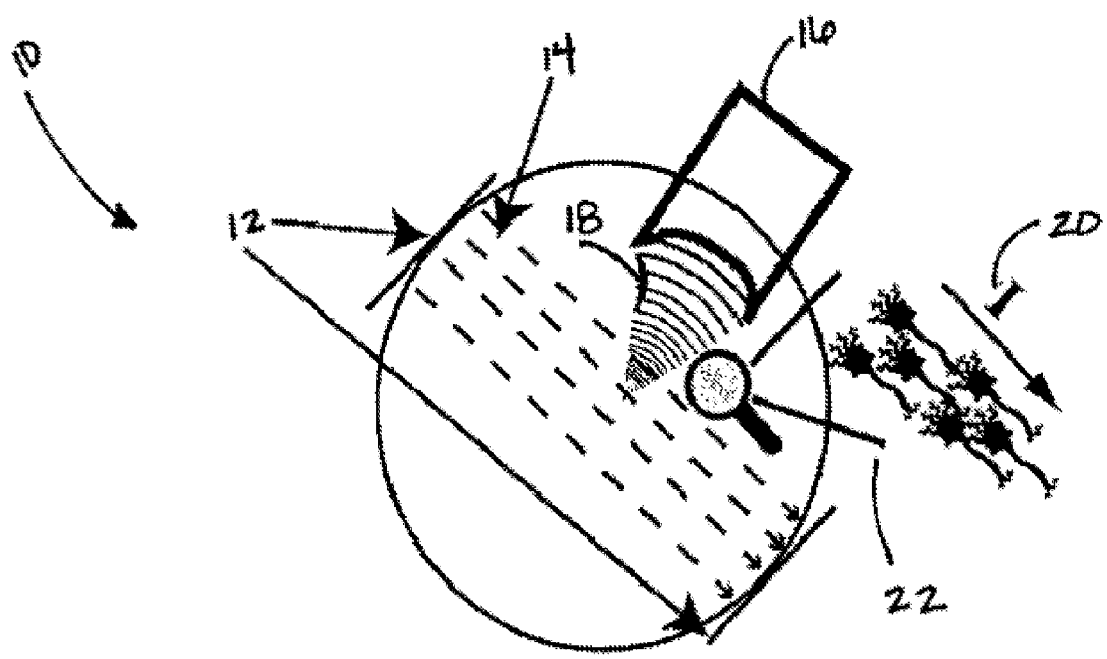
FIG. 1 is a plan view of one embodiment of an apparatus for stimulating biological tissue constructed in accordance with the principles of the present disclosure.

It is envisioned that the present disclosure may be used to stimulate biological tissue in-vivo comprising an electric source that is placed on the body to generate an electric field and a means for altering the permittivity of tissue relative to the electric field, whereby the alteration of the tissue permittivity relative to the electric field generates a displacement current in the tissue. The exemplary embodiments of the apparatuses and methods disclosed can be employed in the area of neural stimulation, where amplified, focused, direction altered, and/or attenuated currents could be used to alter neural activity via directly stimulating neurons, depolarizing neurons, hyperpolarizing neurons, modifying neural membrane potentials, altering the level of neural cell excitability, and/or altering the likelihood of a neural cell firing. Likewise, the method for stimulating biological tissue may also be employed in the area of muscular stimulation, including cardiac stimulation, where amplified, focused, direction altered, and/or attenuated currents could be used to alter muscular activity via direct stimulation, depolarizing muscle cells, hyperpolarizing muscle cells, modifying membrane potentials, altering the level of muscle cell excitability, and/or altering the likelihood of cell firing. Similarly, it is envisioned that the present disclosure may be employed in the area of cellular metabolism, physical therapy, drug delivery, and gene therapy.

Detailed embodiments of the present disclosure are disclosed herein, however, it is to be understood that the described embodiments are merely exemplary of the disclosure, which may be embodied in various forms. Therefore, specific functional details disclosed herein are not to be interpreted as limiting, but merely as a basis for the claims and as a representative basis for teaching one skilled in the art to variously employ the present disclosure in virtually any appropriately detailed embodiment.

The components of the tissue stimulation method according to the present disclosure are fabricated from materials suitable for a variety medical applications, such as, for example, polymerics, gels, films, and/or metals, depending on the particular application and/or preference. Semi-rigid and rigid polymerics are contemplated for fabrication, as well as resilient materials, such as molded medical grade polyurethane, as well as flexible or malleable materials. The motors, gearing, electronics, power components, electrodes, and transducers of the method may be fabricated from those suitable for a variety of medical applications. The method according to the present disclosure may also include circuit boards, circuitry, processor components, etc. for computerized control. One skilled in the art, however, will realize that other materials and fabrication methods suitable for assembly and manufacture, in accordance with the present disclosure, also would be appropriate.

The following discussion includes a description of the components and exemplary methods for generating currents in biological tissues in accordance with the principles of the present disclosure. Alternate embodiments are also disclosed. Reference will now be made in detail to the exemplary embodiments of the present disclosure illustrated in the accompanying figures wherein like reference numerals indicate the similar parts throughout the figures.

Turning now to FIG. 1, which illustrates an exemplary embodiment of an apparatus 10 to alter currents, e.g., amplify, focus, alter direction, and/or attenuate in the presence of an applied electric field or applied current source by the combined application of a mechanical field within a biological material to stimulate the biological cells and/or tissue in accordance with the present disclosure. For example, the apparatus 10 illustrated in FIG. 1 according to the present disclosure may be applied to the area of neural stimulation. An initial source electric field 14 results in a current in the tissue. The electric field 14 is created by an electric source, current or voltage source. As described in further detail below, the permittivity of the tissue is altered relative to the electric field, for example by a mechanical field, thereby generating an additional displacement current.

Electrodes 12 are applied to the scalp and generate a low magnitude electric field 14 over a large brain region. While electrodes 12 are used and applied to the scalp in this exemplary embodiment, it is envisioned that the electrodes may be applied to a number of different areas on the body including areas around the scalp. It is also envisioned that one electrode may be placed proximal to the tissue being stimulated and the other distant, such as one electrode on the scalp and one on the thorax. It is further envisioned that electric source could be mono-polar with just a single electrode, or multi-polar with multiple electrodes. Similarly, the electric source may be applied to tissue via any medically acceptable medium. It is also envisioned that means could be used where the electric source does not need to be in direct contact with the tissue, such as for example, inductive magnetic sources where the entire tissue region is placed within a large solenoid generating magnetic fields or near a coil generating magnetic fields, where the magnetic fields induce electric currents in the tissue.

The electric source may be direct current (DC) or alternating current (AC) and may be applied inside or outside the tissue of interest. Additionally, the source may be time varying. Similarly, the source may be pulsed and may be comprised of time varying pulse forms. The source may be an impulse. Also, the source according to the present disclosure may be intermittent. The electric field source could also work as a component in the imaging process.

A mechanical source such as an ultrasound source 16 is applied on the scalp and provides concentrated acoustic energy 18, i.e., mechanical field to a focused region of neural tissue, affecting a smaller number of neurons 22 than affected by the electric field 14, by the mechanical field 18 altering the tissue permittivity relative to the applied electric field 14, and thereby generating the altered current 20. The mechanical source may be any acoustic source such as an ultrasound device. Generally, such device may be a device composed of electromechanical transducers capable of converting an electrical signal to mechanical energy such as those containing piezoelectric materials, a device composed of electromechanical transducers capable of converting an electrical signal to mechanical energy such as those in an acoustic speaker that implement electromagnets, a device in which the mechanical source is coupled to a separate mechanical apparatus that drives the system, or any similar device capable of converting chemical, plasma, electrical, nuclear, or thermal energy to mechanical energy and generating a mechanical field.

Furthermore, the mechanical field could be generated via an ultrasound device, such as an ultrasound transducer that could be used for imaging tissue. The mechanical field may be coupled to tissue via a bridging medium, such as a container of saline to assist in the focusing or through gels and/or pastes which alter the acoustic impedance between the mechanical source and the tissue. The mechanical field may be time varying, pulsed, an impulse, or may be comprised of time varying pulse forms. It is envisioned that the mechanical source may be applied inside or outside of the tissue of interest. There are no limitations as to the frequencies that can be applied via the mechanical source, however, exemplary mechanical field frequencies range from the sub kHZ to 1000s of MHz. Additionally, multiple transducers providing multiple mechanical fields with similar or differing frequencies, and/or similar or different mechanical field waveforms may be used—such as in an array of sources like those used in focused ultrasound arrays. Similarly, multiple varied electric fields could also be applied. The combined fields, electric and mechanical, may be controlled intermittently to cause specific patterns of spiking activity or alterations in neural excitability. For example, the device may produce a periodic signal at a fixed frequency, or high frequency signals at a pulsed frequency to cause stimulation at pulse frequencies shown to be effective in treating numerous pathologies. Such stimulation waveforms may be those implemented in rapid or theta burst TMS treatments, deep brain stimulation treatments, epidural brain stimulation treatments, spinal cord stimulation treatments, or for peripheral electrical stimulation nerve treatments. The ultrasound source may be placed at any location relative to the electrode locations, i.e., within, on top of, below, or outside the same location as the electrodes as long as components of the electric field and mechanical field are in the same region. The locations of the sources should be relative to each other such that the fields intersect relative to the tissue and cells to be stimulated, or to direct the current alteration relative to the cellular components being stimulated.

The apparatus and method according to the present disclosure generates capacitive currents via permittivity alterations, which can be significant in magnitude, especially in the presence of low frequency applied electric fields. Tissue permittivities in biological tissues are much higher than most other non biological materials, especially for low frequency applied electric fields where the penetration depths of electric fields are highest. This is because the permittivity is inversely related to the frequency of the applied electric field, such that the tissue permittivity magnitude is higher with lower frequencies. For example, for electric field frequencies below 100,000 Hz, brain tissue has permittivity magnitudes as high as or greater than 10^8 (100,000,000) times the permittivity of free space (8.854*10^−12 farad per meter), and as such, minimal local perturbations of the relative magnitude can lead to significant displacement current generation. As the frequency of the electric field increases, the relative permittivity decreases by orders of magnitude, dropping to magnitudes of approximately 10^3 times the permittivity of free space (8.854*10^−12 farad per meter) for electric field frequencies of approximately 100,000 Hz. Additionally, by not being constrained to higher electric field frequencies, the method according to the present disclosure is an advantageous method for stimulating biological tissue due to lowered penetration depth limitations and thus lowered field strength requirements. Additionally, because displacement currents are generated in the area of the permittivity change, focusing can be accomplished via the ultrasound alone. For example, to generate capacitive currents via a permittivity perturbation relative to an applied electric field as described above, broad DC or a low frequency electric source field well below the cellular stimulation threshold is applied to a brain region but stimulation effects are locally focused in a smaller region by altering the tissue permittivity in the focused region of a mechanical field generated by a mechanical source such as an ultrasound source. This could be done noninvasively with the electrodes and the ultrasound device both placed on the scalp surface such that the fields penetrate the tissue surrounding the brain region and intersect in the targeted brain location, or with one or both of the electrodes and/or the ultrasound device implanted below the scalp surface (in the brain or any of the surrounding tissue) such that the fields intersect in the targeted region.

A displacement current is generated by the modification of the permittivity in the presence of the sub threshold electric field and provides a stimulatory signal. In addition to the main permittivity change that occurs in the tissues, which is responsible for stimulation (i.e., the generation of the altered currents for stimulation), a conductivity change could also occur in the tissue, which secondarily alters the ohmic component of the currents. In a further embodiment, the displacement current generation and altered ohmic current components may combine for stimulation. Generally, tissue conductivities vary slightly as a function of the applied electric field frequency over the DC to 100,000 Hz frequency range, but not to the same degree as the permittivities, and increase with the increasing frequency of the applied electric field. Additionally in biological tissues, unlike other materials, the conductivity and permittivity do not show a simple one-to-one relationship as a function of the applied electric field frequency. The permittivity ranges are as discussed above.

Although the process described may be accomplished at any frequency of the applied electric field, the method in an exemplary embodiment is applied with lower frequency applied electric fields due to the fact the permittivity magnitudes of tissues, as high as or greater than 10^8 times the permittivity of free space, and the electric field penetration depths are highest for low frequency applied electric fields. Higher frequency applied electric fields may be less desirable as they will require greater radiation power to penetrate the tissue and/or a more pronounced mechanical source for permittivity alteration to achieve the same relative tissue permittivity change, i.e., at higher applied electric field frequencies the permittivity of the tissue is lower and as such would need a greater overall perturbation to have the same overall change in permittivity of a tissue as at a lower frequency. Applied electric field frequencies in the range of DC to approximately 100,000 Hz frequencies are advantageous due to the high tissue permittivity in this frequency band and the high penetration depth for biological tissues at these frequencies. In this band, tissues are within the so called 'alpha dispersion band' where relative tissue permittivity magnitudes are maximally elevated (i.e., as high as or greater than 10^8 times the permittivity of free space). Frequencies above approximately 100,000 to 1,000,000 Hz for the applied electric fields are still applicable for the method described in generating displacement currents for the stimulation of biologic cells and tissue, however, both the tissue permittivity and penetration depth are limited for biological tissues in this band compared to the previous band but displacement currents of sufficient magnitude can still be generated for some applications. In this range, the magnitude of the applied electric field will likely need to be increased, or the method used to alter the permittivity relative to the applied electric field increased to bring about a greater permittivity change, relative to the tissue's permittivity magnitude for the applied electric field frequency. Additionally, due to potential safety concerns for some applications, it may be necessary to limit the time of application of the fields or to pulse the fields, as opposed to the continuous application that is possible in the prior band. For tissues or applications where the safety concerns preclude the technique in deeper tissues, the technique could still be applied in more superficial applications in a noninvasive manner or via an invasive method. Higher frequency applied electric fields, above 1,000,000 to 100,000,000 Hz, could be used in generating displacement currents for the stimulation of biologic cells and tissue. However, this would require a more sufficient permittivity alteration or electromagnetic radiation, and as such is less than ideal in terms of safety than the earlier bands. For frequencies of the applied electric field above 100,000,000 Hz, biologic cell and tissue stimulation may still be possible, but may be limited for specialized applications that require less significant displacement currents.

The focus of the electric and mechanical fields to generate an altered current according to the present disclosure may be directed to various structures within the brain or nervous system including but not limited to dorsal lateral prefrontal cortex, any component of the basal ganglia, nucleus accumbens, gastric nuclei, brainstem, thalamus, inferior colliculus, superior colliculus, periaqueductal gray, primary motor cortex, supplementary motor cortex, occipital lobe, Brodmann areas 1-48, primary sensory cortex, primary visual cortex, primary auditory cortex, amygdala, hippocampus, cochlea, cranial nerves, cerebellum, frontal lobe, occipital lobe, temporal lobe, parietal lobe, sub-cortical structures, spinal cord, nerve roots, sensory organs, and peripheral nerves.

The focused tissue may be selected such that a wide variety of pathologies may be treated. Such pathologies that may be treated include but are not limited to Multiple Sclerosis, Amyotrophic Lateral Sclerosis, Alzheimer's Disease, Dystonia, Tics, Spinal Cord Injury, Traumatic Brain Injury, Drug Craving, Food Craving, Alcohol Craving, Nicotine Craving, Stuttering, Tinnitus, Spasticity, Parkinson's Disease, Parkinsonianism, Obsessions, Depression, Schizophrenia, Bipolar Disorder, Acute Mania, Catonia, Post-Traumatic Stress Disorder, Autism, Chronic Pain Syndrome, Phantom Limb Pain, Epilepsy, Stroke, Auditory Hallucinations, Movement Disorders, Neurodegenerative Disorders, Pain Disorders, Metabolic Disorders, Addictive Disorders, Psychiatric Disorders, Traumatic Nerve Injury, and Sensory Disorders. Furthermore, electric and mechanical fields to generate an altered current may be focused on specific brain or neural structures to enact procedures including sensory augmentation, sensory alteration, anesthesia induction and maintenance, brain mapping, epileptic mapping, neural atrophy reduction, neuroprosthetic interaction or control with nervous system, stroke and traumatic injury neurorehabilitation, bladder control, assisting breathing, cardiac pacing, muscle stimulation, and treatment of pain syndromes, such as those caused by migraine, neuropathies, and low-back pain; or internal visceral diseases, such as chronic pancreatitis or cancer. The methods herein could be expanded to any form of arthritis, impingement disorders, overuse injuries, entrapment disorders, and/or any muscle, skeletal, or connective tissue disorder which leads to chronic pain, central sensitization of the pain signals, and/or an inflammatory response.

In the focused region of tissue to which the mechanical fields are delivered, the excitability of individual neurons can be heightened to the point that the neurons can be stimulated by the combined fields, or be affected such as to cause or amplify the alteration of the neural excitability caused by the altered currents, either through an increase or decrease in the excitability of the neurons. This alteration of neural excitability can last past the duration of stimulation and thus be used as a basis to provide lasting treatment. Additionally, the combined fields can be provided in multiple, but separate sessions to have a summed, or carry-over effect, on the excitability of the cells and tissue. The combined fields can be provided prior to another form of stimulation, to prime the tissue making it more or less susceptible to alternate, follow-up forms of stimulation. Furthermore, the combined fields can be provided after an alternate form of stimulation, where the alternate form of stimulation is used to prime the tissue to make it more or less susceptible to the form of stimulation disclosed herein. Furthermore, the combined fields could be applied for a chronic period of time.

Figure 2:
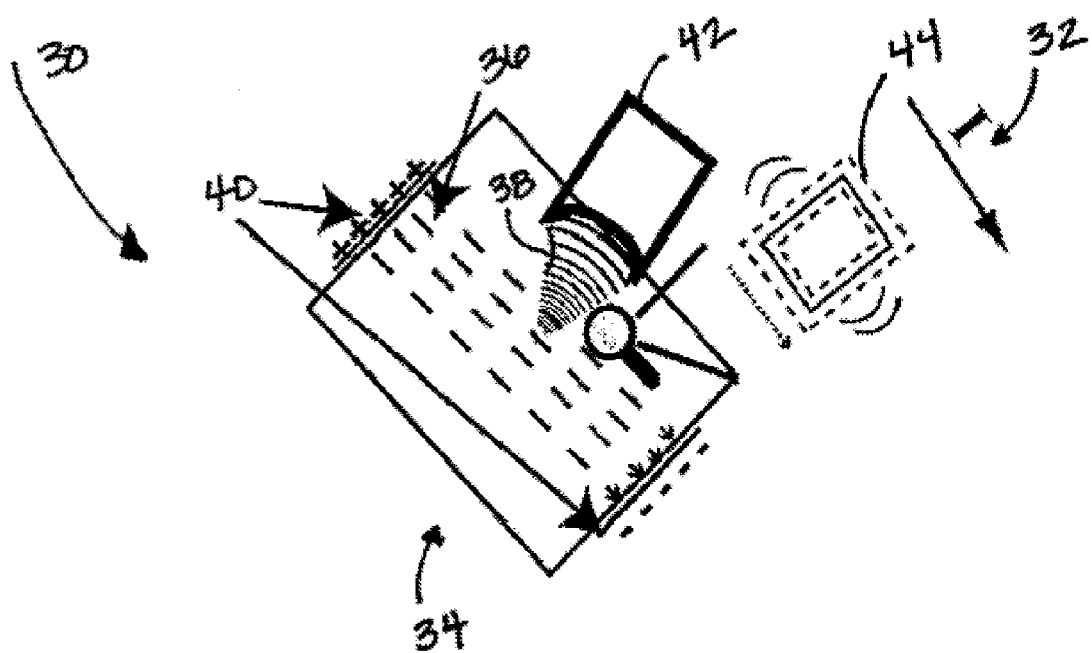
FIG. 2 is a top plan view of an exemplary embodiment of an apparatus for stimulating biological tissue constructed in accordance with the principles of the present disclosure.

FIG. 2 illustrates a set up 30 to perform a method for generating an altered current with a newly generated displacement current 32 for stimulation in biologic tissue 34 through the combined effects of an electric field 36 and a mechanical field 38. A tissue or composite of tissues 34 is placed adjacent to the anode and cathode of an electric source 40 which generates an electric field 36. The electric field 36 is combined with a mechanical, e.g., ultrasound field 38 which can be focused on the tissue 34 and generated via an ultrasound transducer 42. In a sub-region of tissue 44 where the mechanical field 38 is focused and intersects with the electric field 36, a displacement current 32 is generated. By vibrating and/or mechanically perturbing the sub-region of tissue 44, the permittivity of the tissue 44 can be altered relative to the applied electric field 36 to generate a displacement current 32 in addition to the current that would be present due to the source electric field 36 and altered due to conductivity changes in the tissue caused by the mechanical perturbation.

By providing the mechanical field 38 to the sub region of tissue 44, the permittivity can be altered within the electric field 36 by either new elements of the sub region of tissue 44 vibrating in and out of the electric field such that the continuum permittivity of the tissue is changed relative to the electric field 36, or that the bulk properties of the sub region of tissue 44 and the permittivity, or tissue capacitance, change due to the mechanical perturbation. An example of altering the permittivity within the electric field can occur when a cell membrane and extra-cellular fluid, both of different permittivities, are altered in position relative to the electric field by the mechanical field. This movement of tissues of different permittivity relative to the electric field will generate a new displacement current. The tissues could have permittivity values as high as or greater than $10^8$ times the permittivity of free space, differ by orders of magnitude, and/or have anisotropic properties such that the tissue itself demonstrates a different permittivity magnitude depending on the relative direction of the applied electric field. An example of altering permittivity of the bulk tissue occurs where the relative permittivity constant of the bulk tissue is directly altered by mechanical perturbation in the presence of an electric field. The mechanical source, i.e., ultrasound source may be placed at any location relative to the electrode locations, i.e., within or outside the same location as the electrodes, as long as components of the electric field and mechanical field are in the same region.

Tissue permittivities can be altered relative to the applied electric fields via a number of methods. Mechanical techniques can be used to either alter the bulk tissue permittivity relative to an applied electric field or move tissue components of differing permittivities relative to an applied electric field. There are no specific limitations to the frequency of the mechanical field that is applied as previously discussed, however, exemplary frequencies range from the sub kHZ to 1000s of MHz. A second electromagnetic field could be applied to the tissue, at a different frequency than the initial frequency of the applied electromagnetic field, such that it alters the tissue permittivity at the frequency dependent point of the initially applied electric field. An optical signal could also be focused on the tissues to alter the permittivity of the tissue relative to an applied electric field. A chemical agent or thermal field could also be applied to the tissues to alter the permittivity of the tissue relative to an applied electric field. These methods could also be used in combination to alter the tissue permittivity relative to an applied electric field via invasive or noninvasive methods.

For example, FIG. 3 shows a set up 50 for generating an altered current with a newly generated displacement current 52 through the combined effects of an electric field 54 and a chemical agent 56. A tissue or composite of tissues 58 is placed within an electric source 60 which generates an electric field 54 and combined with chemical source 62 which releases a chemical agent 56 that can be focused on the tissue 58. In the area that the chemical agent 56 is released in the tissue 64, the electric field 54 transects the sub region of tissue 64, and the chemical agent 56 reacts with the sub region of tissue 64 to alter the tissue's relative permittivity relative to the applied electric field 54. This generates a displacement current 52 in addition to the current that would be present due to the source electric field 54. The chemical agent 56 may be any agent which can react with the tissue or cellular components of the tissue 64 to alter its permittivity relative to the electric field 54. This may be by a thermoreactive process to raise or lower the tissue 64 temperature or through a chemical reaction which alters the distribution of ions in the cellular and extra-cellular media, for instance, along ionic double layers at cell walls in the tissue 64. Similarly, the conformation of proteins and other charged components within the tissue 64 could be altered such that the permittivity of the tissue is altered relative to the low frequency electric field 54. The agent could also be any agent that adapts the permanent dipole moments of any molecules or compounds in the tissue 64, temporarily or permanently relative to the low frequency electric field 54. The chemical reaction driven by the chemical agent 56 must work rapidly enough such that the permittivity of the tissue is quickly altered in the presence of the electric field 54 in order to generate the displacement current 52. The reaction may also be such as to fluctuate the permittivity, such that as the permittivity continues to change displacement currents continue to be generated. In addition to the main permittivity change that occurs in the tissues, a conductivity change could also occur in the tissue, which secondarily alters the ohmic component of the currents. A biological agent may be used in place of, or in addition to, the chemical agent 56. This embodiment may have particular application for focused drug delivery where an additional chemical or biological agent is included to assist in therapy of the tissue, or where the altered current could drive an additional electrochemical reaction for therapy. For example, this could be used in areas such as focused gene therapy or focused chemotherapy.

Another example is shown in FIG. 4, which illustrates a set up 70 for applying a method for generating an altered current with a newly generated displacement current 72 through the combined effects of a low frequency electric field 74 and an electromagnetic radiation field 76. A tissue or composite of tissues 78 is placed within a low frequency electric field 74 which is generated by an electric source 80 and combined with radiation source 82 which generates a radiation field 76 that can be focused on the tissue 78. In the area that the radiation field 76 is focused in the tissue 78, the electric field 74 transects the sub component of tissue 84, where the radiation field 76 interacts with the sub component of tissue 84 to alter the tissue's relative permittivity relative to the applied electric field 74, and as such generates a displacement current 72 in addition to the current that would be present due to the source electric field 74 or the radiation source field 76 alone. The electromagnetic radiation field 76 could, for example, interact with the tissue 84 by altering its temperature through ohmic processes, alter the distribution of ions in the cellular and extra-cellular media for instance along ionic double layers along cell walls through the electric forces acting on the ions, or alter the conformation of proteins and other charged components within the tissue through the electric forces such that the permittivity of the tissue is altered relative to the low frequency electric field 74. Furthermore, the electromagnetic field 76, could interact with the tissue 84 by moving components of the tissue via electrorestrictive forces, as would be seen in anisotropic tissues, to alter the continuum permittivity of the tissue relative to the low frequency electric field 74. In addition to the main permittivity change that occurs in the tissues, a conductivity change could also occur in the tissue, which secondarily alters the ohmic component of the currents.

FIG. 5 shows a set up 90 for applying a method for generating an altered current with a newly generated displacement current 92 through the combined effects of an electric field 94 and an optical beam 96. A tissue or composite of tissues 98 is placed within electric field 94 generated by an electric source 100 and combined with optical source 102 which generates optical beam 96 that can be focused on the tissue 98. In the area that the optical beam 96 is focused on the tissue, the electric field 94 transects the sub component of tissue 104, where the optical beam 96 reacts with the tissue to alter the tissue's relative permittivity relative to the applied electric field 94, and as such generates a displacement current 92 in addition to the current that would be present due to the source electric field 94. The optical beam 96 could, for example, interact with the tissue by altering its temperature through photothermal effects and/or particle excitation, alter the distribution of ions in the cellular and extra-cellular media for instance along ionic double layers along cell walls by exciting the movement of ions optically, ionizing the tissue via laser tissue-interactions, or alter the conformation of proteins and other charged components within the tissue such that the permittivity of the tissue is altered relative to the low frequency electric field 94. In addition to the main permittivity change that occurs in the tissues, a conductivity change could also occur in the tissue, which secondarily alters the ohmic component of the currents.

In another embodiment, a thermal source to alter the permittivity of the tissue may be used. In such embodiments, a thermal source such as a heating probe, a cooling probe, or a hybrid probe may be placed external or internal to the tissue to be stimulated. A thermal source may alter the permittivity of the tissue through the direct permittivity dependence of tissue temperature, mechanical expansion of tissues in response to temperature changes, or by mechanical forces that arise due to altered particle and ionic agitation in response to the temperature alteration such that permittivity of the tissue is altered relative to an applied electric field. In addition to the main permittivity change that occurs in the tissues, a conductivity change could also occur in the tissue, which secondarily alters the ohmic component of the currents. This embodiment may be useful for stimulation in the presence of an acute injury to the tissue where the thermal source could be used to additionally assist in the treatment of the tissue injury, for example with a traumatic brain injury or an infarct in any organ such as the heart. The tissue could be cooled or heated at the same time stimulation is provided to reduce the impact of an injury.

In a further embodiment, the method according to the present disclosure is applied in the area of muscular stimulation, where amplified, focused, direction altered, and/or attenuated currents could be used to alter muscular activity via direct stimulation, depolarizing muscular cells, hyperpolarizing muscular cells, modifying membrane potentials, and/or increasing or decreasing the excitability of the muscle cells. This alteration of excitability or firing patterns can last past the duration of stimulation and thus be used as a basis to provide lasting treatment. Additionally, the stimulation can be provided in multiple, but separate sessions to have a summed, or carry-over effect, on the excitability of cells and tissue. Additionally, the stimulation could be provided to prime the tissue by adjusting the muscle cell excitability to make it more or less susceptible to alternate follow up forms of stimulation. The stimulation could be used after another form of stimulation was used to prime the tissue. Furthermore, the stimulation could be applied for a chronic period of time. This embodiment may be useful for altering or assisting cardiac pacing or function, assisted breathing, muscle stimulation for rehabilitation, muscle stimulation in the presence of nerve or spinal cord injury to prevent atrophy or assist in movement, or as substitution for physical exercise.

In yet another embodiment, the method according to the present disclosure can be applied the area of physical therapy, where amplified, focused, direction altered, and/or attenuated currents could be used to stimulate blood flow, increase or alter neuromuscular response, limit inflammation, speed the break down of scar tissue, and speed rehabilitation by applying the focus of the current generation to the effected region in need of physical therapy. It is envisioned that the method according to the present disclosure may have a wide variety in the area of physical therapy including the treatment or rehabilitation of traumatic injuries, sports injuries, surgical rehabilitation, occupational therapy, and assisted rehabilitation following neural or muscular injury. For instance, following an injury to a joint or muscle, there is often increased inflammation and scar tissue in the region and decreased neural and muscular response. Typically, ultrasound is provided to the affected region to increase blood flow to the region and increase the metabolic re-absorption of the scar tissue while electrical stimulation is provided separately to the nerves and muscles; however, by providing them together, a person could receive the benefit of each individual effect, but additionally amplified stimulatory and metabolic effects through the altered currents. The other methods for generating altered currents discussed within could also be used to assist in physical therapy via the displacement currents that are generated.

Furthermore, the method according to the present disclosure may be applied to the area of cellular metabolism, where currents could be used to interact with electrically receptive cells or charged membranes to alter the tissue or cellular dynamics. It is envisioned that this embodiment could provide treatment for various diseases where electrically receptive cells respond to the newly generated displacement currents and altered current distribution.

Furthermore, the method according to the present disclosure may be applied to the area of gene therapy. Amplified, focused, direction altered, and/or attenuated currents could be used to interact with electrically receptive cells or receptors within the cell to influence protein transcription processes and alter the genetic content of the cells. The altered current densities in the tissue can interact with the tissue to stimulate this altered gene regulation. Additionally, the displacement currents generated by the method could further be used to assist in drug delivery and/or gene therapy through the altered current influence on the delivery of agents.

In certain embodiments, the invention relates to apparatuses and methods for stimulating and monitoring biological tissue. Any type of stimulation known in the art may be used with methods of the invention, and the stimulation may be provided in any clinically acceptable manner. For example, the stimulation may be provided invasively or noninvasively. Preferably, the stimulation is provided in a noninvasive manner. For example, electrodes may be configured to be applied to the specified tissue, tissues, or adjacent tissues. As one alternative, the electric source may be implanted inside the specified tissue, tissues, or adjacent tissues.

Exemplary types of stimulation include mechanical, optical, electromagnetic, thermal, or a combination thereof. In particular embodiments, the stimulation is a mechanical field (i.e., acoustic field), such as that produced by an ultrasound device. In other embodiments, the stimulation is an electrical field. In other embodiments, the stimulation is an magnetic field. Other exemplary types of stimulation include Transcranial Direct Current Stimulation (TDCS), Transcranial Ultrasound (TUS)/Transcranial Doppler Ultrasound (TDUS), Transcranial Electrical Stimulation (TES), Transcranial Alternating Current Stimulation (TACS), Cranial Electrical Stimulation (CES), or Transcranial Magnetic Stimulation (TMS). Other exemplary types include implant methods such as deep brain stimulation (DBS), microstimulation, spinal cord stimulation (SCS), and vagal nerve stimulation (VNS). In other embodiments, the stimulation source may work in part through the alteration of the nervous tissue electromagnetic properties, where stimulation occurs from an electric source capable of generating an electric field across a region of tissue and a means for altering the permittivity of tissue relative to the electric field, whereby the alteration of the tissue permittivity relative to the electric field generates a displacement current in the tissue. The means for altering the permittivity may include a chemical source, optical source, mechanical source, thermal source, or electromagnetic source.

In other embodiments, the stimulation is provided by a combination of an electric field and a mechanical field. The electric field may be pulsed, time varying, pulsed a plurality of time with each pulse being for a different length of time, or time invariant. Generally, the electric source is current that has a frequency from about DC to approximately 100,000 Hz. The mechanical field may be pulsed, time varying, or pulsed a plurality of time with each pulse being for a different length of time. In certain embodiments, the electric field is a DC electric field.

In other embodiments, the stimulation is a combination of Transcranial Ultrasound (TUS) and Transcranial Direct Current Stimulation (TDCS). Such a combination allows for focality (ability to place stimulation at fixed locations); depth (ability to selectively reach deep regions of the brain); persistence (ability to maintain stimulation effect after treatment ends); and potentiation (ability to stimulate with lower levels of energy than required by TDCS alone to achieve a clinical effect).

In certain embodiments a medical imaging modality may be combined with stimulation. Exemplary imaging modalities include magnetic resonance imaging (MRI), functional MRI (fMRI), ultrasound, positron emission tomography (PET), single photon emission computed tomography (SPECT), computer aided tomography scan (CAT-scan), XRAY, optical coherence tomography (OCT), diffusion tensor imaging (DTI), diffusion spectrum imaging (DSI), electro-acoustic imaging, electromagnetic based imaging, electro-encephalogram (EEG), electromyogram (EMG), high density EEG, spectroscopy based methods, electrocardiogram (EKG) electrical based imaging, magnetic based imaging, nuclear based imaging, optical (photonic) based imaging, mechanical based imaging, thermal based imaging, combined imaging modalities, imaging with contrast agents, imaging without contrast agents, etc. In other embodiments, physiological measurements, stimulation subject assessment measures, and/or biofeedback measures are combined with stimulation.

The imaging modalities, physiological measurements, stimulation subject assessment measures, and/or biofeedback measures could be used to assist in the stimulation by aiding in the targeting (localizing) of stimulation, dosing of stimulation, characterizing safety parameters, analyzing the online or offline effects of stimulation, and/or maximizing the therapeutic effect of stimulation. This facilitation could also be done by altering or controlling the stimulation source(s), field parameters, and/or the stimulation interface apparatus parameters.

In terms of targeting tissues to stimulate, the targeted region can be imaged with any imaging modality that provides anatomical information about the region. That image could then be used to determine the placement of the stimulation source. For example, with an electrosonic (electrical source and mechanical (i.e., sonic/ultrasound), note electrosonic is used synomously with electromechanical herein) approach one would determine the placement of the electrical source and the ultrasound source to target the desired regions, either directly or within an interface apparatus.

The imaging information could also be used to provide guidance for the design and property tuning of an interface apparatus between the subject to be stimulated and the stimulation source(s). For example, one might simply determine the placement of the source(s) of stimulation and/or the properties of the interface apparatus between the stimulation patient and the device (such as for example the dimensions, materials impedances, and/or design criteria) based on anatomical landmarks determined from the image and predetermined source characteristics (such as for example the beam profile of an ultrasonic transducer and the predicted field distribution of an electric field source). Further information is described in Wagner et al. (U.S. patent application number 2010/0070006), the content of which is incorporated by reference herein in its entirety.

Additionally, the implementation of an imaging system for targeting could also be used to direct the source fields necessary for stimulation based on calculations developed from the imaging information (or to calculate the field to correlate to stimulation effects following stimulation) and/or physiological measurements, stimulation subject assessment measures, and/or biofeedback measures. An imaging modality could be used to identify the tissue distribution of the subject to be stimulated, from which tissue boundaries in the stimulation area can be identified. This tissue and/or boundary identification could be pursued with any image analysis algorithm, and could be completed prior to stimulation, during stimulation, or following stimulation.

Once the tissues are identified, a 'computational mesh' can be built to capture the tissue segmentation demonstrated in the images, where mesh components can be assigned any physical and/or chemical characteristic of which will be used in determining targeting and localization of the fields, chemicals, and/or stimulation effects (e.g., material properties, electromagnetic properties, thermodynamic properties, mechanical/acoustic properties, optical properties, chemical properties, etc). These properties could be assigned known values determined before stimulation, with values determined during stimulation, or with values determined following stimulation.

Following the generation of a computational mesh based on the tissue properties (and geometry) to be modeled, models can be generated with computational/numerical solvers that capture the physics and/or chemistry of the underlying system such as by also including the source and/or interface properties (position, size, shape, and/or material properties) and/or source field characteristics (amplitude, waveform (shape/timing dynamics), frequency (power components and/or pulse frequencies if using pulsed field), and/or timing information) and/or chemical agent characteristics (concentrations, distributions, compositions, kinetics, and/or additional information).

This can be used to determine the driving field's focus, orientation, focality, and overall distribution in the tissues to be stimulated (such as for example one could determine the electrical field, voltage, current density, magnetic field, force field, mechanical field (acoustic field), pressure field, tissue acceleration, tissue position, tissue velocity, tissue temperature, etc) or the chemical reactions and/or chemistry effects that are modeled (kinetics, chemical distributions, reactions, etc) in the tissue(s) to be stimulated. For a method where tissue properties are modified relative to an applied electric field to generate a new current, this information could then be used to calculate the altered tissue electromagnetic properties (and/or relative positions) relative to the applied electrical field in the tissue(s) to be stimulated, such that one can calculate the newly generated current density and/or electrical field distributions (such calculations can be made with any particular means for altering the tissue electromagnetic properties (including but not limited to mechanical, thermal, electromagnetic, and optical means) in the tissue(s) to be stimulated. Additionally, this information could also be used to guide the placement, design, material properties, and/or modification of an interface mechanism.

Ultimately this can allow for pre, during, or post stimulation targeting/localization via calculations based on the initial imaging modality, tissue characteristics, field source characteristics, and/or the properties of the interface apparatus (and/or the source characteristics of the means that alters the electromagnetic properties of the tissue to be stimulated from combined methods where new currents are generated relative to an electric field source). These methods could be implemented with any form of stimulation, including but not limited to electromagnetic, mechanical (i.e., acoustic), optical, thermal, electrical, magnetic, and/or combined methods (and/or methods which alter tissue impedances relative to electrical sources to generate altered stimulation currents, for example with electromagnetic, mechanical (i.e., acoustic), optical, thermal, electrical, magnetic, and/or combined sources).

In one particular example, in the area of brain stimulation, with an electrical source generating an applied electrical field and/or ultrasound (i.e, mechanical) source generating focused acoustic energy on the tissue area to be stimulated, the electrical field distribution and/or the mechanical field distribution can be calculated based on the relative electrical field and mechanical field transducer source characteristics (transducer position(s), transducer size(s), transducer shape (s), field frequencies, field time dynamics, field amplitudes, field phase information, etc) to anatomical tissue distribution (with the appropriate tissue characteristics (for example the electromagnetic properties and tissue mechanical/acoustic properties)) which can be determined from any imaging methodology which provides anatomical information about the area to be stimulated (such as for example a CAT-scan or and MRI) and/or with predetermined tissue characteristics (and/or also with values which at least in part could be determined via an imaging modality, such as conductivity characteristics based on DTI images); for example one might solve a modified Laplacian, $$\nabla \cdot \left( \frac{\partial (\varepsilon \nabla \Phi)}{\partial t} + \sigma \nabla \Phi \right) = 0,$$

for the an electrical potential (where $\Phi$ is solved in the sinusoidal steady state for particular angular frequency, $\omega$, of the electrical source for particular permittivities, $\in$, and conductivities, $\sigma$, of the tissues being examined (as functions of the frequency of the stimulation electrical field)) based on a particular electrical source, and the Westervelt equation:

$$\nabla^2 p - \frac{1}{c^2} \frac{\partial^2 p}{\partial t^2} + \frac{\delta}{c^4} \frac{\partial^3 p}{\partial t^3} + \frac{\beta}{\rho c^4} \left[ p \frac{\partial^2 p}{\partial t^2} + \left( \frac{\partial p}{\partial t} \right)^2 \right] - \nabla p \cdot \nabla (\ln \rho) = 0$$

for a particular mechanical source (where p is pressure, and c is the speed of sound, $\delta$ is acoustic diffusivity, $\beta$ is the coefficient of nonlinearity, and $\rho$ is the density of the respective tissues), and the appropriate boundary conditions between varied tissues. The calculated electrical and mechanical field distributions can be used to calculate the altered tissue electromagnetic properties (and/or relative tissue positions (with varied tissue electromagnetic properties)) relative to the applied electrical field, such that one can calculate the newly generated current density and/or electrical field distributions; for example one could pursue tissue/field perturbation model and/or a hybrid Hinch/Fixman (Chew; Fixman 1980; Chew and Sen 1982; Fixman 1982; Hinch, Sherwood et al. 1983) inspired model of dielectric enhancement to determine field perturbations and changes in bulk permittivity, thus ultimately calculating the current density distributions in the brain during stimulation (where J=$\sigma$E+$\partial$($\in$E)/$\partial$t, J is the current in the tissue, $\sigma$ the tissue conductivity, E the total field (i.e., source plus perturbation field), and $\in$ is the tissue permittivity; in regions outside of the main focus fields could be determined through continuity equations).

This information will in turn allow one to predict the distribution of the fields and/or currents in the brain based on the imaging and stimulation source information and thus predict locations of effect of stimulation (and/or magnitude of effect). If one chose to use an interface apparatus during the stimulation, such as a helmet like mechanism, the helmet itself could be tailored uniquely for a subject being stimulated based on the calculated field and/or targeting information (such as where one could integrate the helmet design and materials into all of the subsequent physics (and chemical) based calculations). This information and/or resulting calculations could also be integrated with physiological measurements, stimulation subject assessment measures, and/or biofeedback measures, as it could be used to assist in the stimulation by aiding in the targeting (localizing) of stimulation, dosing of stimulation, characterizing safety parameters, and/or analyzing the online or offline effects of stimulation. This facilitation can also be done by altering or controlling the stimulation source(s), field parameters, and/or the stimulation interface apparatus parameters (based on the calculations and/or other feedback information).

One could implement a closed loop system which could automatically tune stimulation based on the calculations and/or feedback which is gathered and fed into an automated control system(s) to tune stimulation results to a desired response based on a particular algorithm and/or an adaptive system; one could implement a system which allows a person or persons operating the stimulation system to modify the stimulation system itself to achieve a desired response relative to the information/feedback that is gathered; and/or a hybrid system of control (note that the information/feedback can be gained from any imaging modalities, biofeedback, physiological measures, and/or other measures as exemplified above). Accordingly, these methods could be implemented with any stimulation method by adapting the physical field calculations appropriately (for example electrical field sources and effects could be calculated with the modified Laplacian equation or TUS acoustic fields could be solved with the Westervelt equation alone (one could also calculate local field changes based on sources of electrical fields such charged protiens, membranes, and macromolecules, similar to the methods outlined above).

These methods could be implemented with any form of stimulation. Exemplary types of stimulation include mechanical, optical, electromagnetic, thermal, or a combination thereof. In particular embodiments, the stimulation is a mechanical field (i.e., acoustic field), such as that produced by an ultrasound device. In other embodiments, the stimulation is an electrical field. In other embodiments, the stimulation is a magnetic field. Other exemplary types of stimulation include Transcranial Direct Current Stimulation (TDCS), Transcranial Ultrasound (TUS)/Transcranial Doppler Ultrasound (TDUS), Transcranial Electrical Stimulation (TES), Transcranial Alternating Current Stimulation (TACS), Cranial Electrical Stimulation (CES), or Transcranial Magnetic Stimulation (TMS). Other exemplary types include implant methods such as deep brain stimulation (DBS), microstimulation, spinal cord stimulation (SCS), and vagal nerve stimulation (VNS). In other embodiments, the stimulation source may work in part through the alteration of the nervous tissue electromagnetic properties, where stimulation occurs from an electric source capable of generating an electric field across a region of tissue and a means for altering the permittivity of tissue relative to the electric field, whereby the alteration of the tissue permittivity relative to the electric field generates a displacement current in the tissue. The means for altering the permittivity may include a chemical source, optical source, mechanical source, thermal source, or electromagnetic source.

Stimulation targeting, localization, and/or field information could also be integrated with additional technologies. For instance, one could integrate the imaging based field solver methodologies with frameless stereotactic systems to track/target stimulation location during a procedure. Additionally, as this targeting, localization, and/or field information can be used to predict the strength and orientation of the current densities (and/or other fields) generated in the tissues relative to the tissue to be stimulated, this information can in turn be fed into neural modeling algorithms (such as Hodgkin and Huxley based stimulation models) that can be used to predict the neural response and/or the information can be used to guide dosing of stimulation. Additionally, the information could be used to adjust the parameters of stimulation and or the characteristics of the interface.

Imaging modalities, physiological measurements, stimulation subject assessment measures, and/or biofeedback measures can also be used to track the effect of stimulation, and ultimately be integrated with the stimulator and/or a interface apparatus to provide a closed loop system of controlled stimulation (and/or with the targeting/field information described above). Imaging modalities that provide information such as but not limited to tissue electrical activity (such as for example, EEG data from the brain for neural stimulation or EKG information from the heart for cardiac stimulation or EMG data from muscle during neural and/or muscle stimulation or electro-retinal gram (ERG) data for visual system stimulation), tissue metabolic information (such as from glucose information from a fluorodeoxyglucose (FDG) based PET scan), tissue blood flow/absorption (such as blood flow information that might be determined from a BOLD signal that might be determined during MRI or with modified functional measures), neuroreceptor activation (such as through radioligands that bind to dopamine receptors and can be imaged with modalities such as PET), tissue temperature changes (such as from thermal imaging), and/or any information of tissue response could be integrated with the stimulation method to provide system based feedback and provide guidance to hone stimulation field parameters such as the stimulation duration, stimulation waveform shape (amplitude and dynamics); source position, size, shape relative to tissues to be stimulated; and/or stimulation targeting, localization, and/or field parameters, such as the source fields timing dynamics, amplitude and orientation. Such imaging modalities, used to track the effect of stimulation, could also be integrated with methods elaborated on above to assist in targeting and dosing calculations.

Similarly physiological measurements such as but not limited to heart rate, respiratory rate, blood gas levels, blood pressure, respiratory gas compositions, urine and fluid concentrations, blood chemistry (including hormone levels), electrolyte levels, pain markers, stress indicators, joint function measures (e,g, mobility, strength, range of motion), patient weight, sensory markers, auditory measures, perceptual measures, emotional markers, skin conductance (i.e., sweat level), pupil dilation, emotional markers, temperature, fluid levels, body/limb position, fatigue markers, fear markers, coordination measures, psychiatric markers, addiction markers, motor performance measures, and/or eye position/movement could be also integrated with the stimulation method to provide system based feedback and provide guidance to hone stimulation field parameters such as the stimulation duration, stimulation waveform shape (amplitude and dynamics); source position, size, shape relative to tissues to be stimulated; and/or stimulation targeting, localization, and/or field parameters, such as the source fields timing dynamics, amplitude and orientation.

Such physiological measurements, used to track the effect of stimulation, could also be integrated with methods elaborated on above to assist in targeting and dosing calculations. Additionally, one could use other biofeedback or stimulation subject assessment information directly gathered from the subject being stimulated such as but not limited to task performance (such as a motor performance, memory, or learning task), subject response (such as to depression based questionnaire/metrics to assess mood), pain measures (such as pain assessment levels or amount of pain killers used), addiction measures (such as alcohol consumption or drug use), subject gathered reports, subject based observations, and/or any subject based self assessments could be also integrated with the stimulation method to provide system based feedback and provide guidance to hone stimulation field parameters such as the stimulation duration, stimulation waveform shape (amplitude and dynamics); source position, size, shape relative to tissues to be stimulated; and/or stimulation targeting, localization, and/or field parameters, such as the source fields timing dynamics, amplitude and orientation. Such measures, used to track the effect of stimulation, can also be integrated with methods elaborated on above to assist in targeting and dosing calculations.

One could tune/adjust such things as the stimulation source(s) position(s), size(s), and/or shape(s) relative to the tissue to be stimulated (such as the electrodes for generating the electric fields, transducers for generating acoustic fields, and/or the source of the means for modifying the electromagnetic parameters of tissues to be stimulated (i.e., mechanical/acoustic field source/transducer, optical source, thermal source, chemical source, and/or a secondary electromagnetic field source)); the field(s) that are generated from sources in terms of magnitude, direction, waveform dynamics, frequency characteristics (power spectrum of waveform and/or potential pulse frequency of stimulation field waveforms), phase information, and/or the duration of application; and/or chemical processes (duration, kinetics, chemical concentrations, distributions, etc) driven by sources.

Additionally, imaging modalities, physiological measures, biofeedback measures, stimulation subject assessments, and/or other measures might not just be integrated with the process that stimulates tissues through the combined application of electrical and/or mechanical fields (and/or chemical agents, thermal fields, optical fields/beams, and/or secondary electromagnetic fields), but effectively they could also be integrated with an interfacing apparatus to increase the interface apparatus's efficiency or modify its use relative to the measures outlined above such as but not limited to altering the material properties of the interface (such as for example altering the electrical impedance of a component(s) of the interface or altering a mechanical/acoustic properties of a component(s) of the interface mechanism such as the acoustic impendence); alter the interface apparatus position, size, shape, and/or position; alter the components of the stimulation process that it stores or interfaces with (such as in size, shape, and/or position; for example the source of the electric field and/or means to alter the tissue electromagnetic properties for tissue stimulation); altering composition(s) of the material(s) within and/or on the interface (such as fluid concentrations to couple a mechanical source with tissues to be stimulated); to control the number of uses of the interface (or the duration of its use); and/or any adjustable quality as described above in the interface description.

These modifications can be made before a stimulation session (based on previously obtained/analyzed information), during stimulation (with real time or online information), or following stimulation for subsequent stimulation sessions (with data analyzed following stimulation). One could also adjust/tune the stimulation parameters based on the information acquired before stimulation not compared to anything, during stimulation (online) compared to the pre-stimulation baseline, inter-stimulation session comparisons, cross stimulation session comparisons, pre vs. post stimulation comparisons, across multiple samples (such as across patient populations with averaged data), and/or any combination or permutation in which the data is obtained and/or analyzed. These methods could be implemented with any form of stimulation, including but not limited to electromagnetic, acoustic, optical, thermal, electrical, magnetic, and/or combined methods (and/or methods which alter tissue impedances relative to electrical sources to generate altered stimulation currents, for example with electromagnetic, acoustic, optical, thermal, electrical, magnetic, and/or combined sources).

One could implement a closed loop system which could automatically tune stimulation based on the information/feedback which is gathered and fed into an automated control system(s) to tune stimulation results to a desired response based on a particular algorithm and/or an adaptive system; one could implement a system which allows a person or persons operating the stimulation system to modify the stimulation system itself to achieve a desired response relative to the information/feedback that is gathered; and/or a hybrid system of control (note that the information/feedback can be gained from any imaging modalities, biofeedback, physiological measures, and/or other measures as exemplified above).

For example in the area of brain stimulation, with an electromechanical (i.e., electrosonic) based stimulator, with an electrical source providing a primary electric field and an acoustic source providing focused acoustic energy, one could set up a system such that source electrodes for generating the primary electric field can have their size, shape, and/or position modified in real time as directed by imaging information (and/or any other type of information) that is being gathered during stimulation. Similarly, one could set up a system such that a source transducer for generating an acoustic field can have its shape (and/or size) modified in real time and/or have its position changed in real time as guided by imaging information (and/or any other type of information) that is being gathered during stimulation.

Similarly the fields that are generated by these sources can have their amplitude, waveform dynamics/timing, frequency characteristics, phase characteristics, distribution, duration, direction, and/or orientation altered as directed by imaging information (and/or any other type of information) that is being gathered before, during, or after stimulation. Similarly if an interface apparatus is being used, it could have any of characteristics altered (size, shape, position, material properties, source contained positions (sizes and/or shapes), etc), such as for example part of its electrical impedance altered such that an electrical field that is targeting underlying tissue could be redirected to another tissue location as guided by imaging information (and/or any other type of information) that is being gathered during stimulation. For example, one could provide electromechanical stimulation (electrical field combined with a mechanical field) to a subject's brain while simultaneously recording the EEG response, and subsequently use the EEG imaging information as a guide to neural response to guide an algorithm which controls the alteration the electromechanical stimulation parameters (for example the source position, field amplitudes, stimulation waveform, stimulation duration, etc) of the electrical and mechanical field sources to tune the desired EEG response (For example one could analyze the power and/or frequency information in the EEG signal relative to stimulation provided, and in turn adjust the stimulation parameters relative to the EEG signal (such as for example, the amplitude and/or frequency properties of the mechanical and electrical source generated fields could be adjusted relative to the real time EEG response).

Alternatively, for example, one could adjust the location of the source positions along a stimulation subject's scalp, based on field calculations made as explained above, but additionally tuned with functional MRI (fMRI) information depicting location effects of stimulation, and further integrated with real time EEG data). The stimulation parameters could simply be modified by a person administering the stimulation, or be automatically controlled through a computer/machine based feedback control system during stimulation (essentially making a closed loop system), and/or a hybrid system of control. Or furthermore, the interface between the electrical field source and/or the acoustic field source could be modified through the controlled feedback system to aid in targeting or to optimae the therapeutic effect of stimulation.

Additionally, imaging modalities, physiological measures, biofeedback measures, stimulation subject assessments, and/or other measures might also be used to monitor safety parameters in the tissue before, during, and/or after stimulation (either via calculations based on the imaging and source information, and/or measured information alone). For instance one could use the thermal information to assure tissue temperatures remain within desired levels, electrical activity information to assess for potential seizure activity or abnormal neural response, current density magnitude calculations in the tissue (including a breakdown of the current types (i.e., ohmic vs. capacitive)) to determine if stimulation currents are within appropriate safety windows, psychological measures from a stimulation subject response (such as for example markers for depression and/or mood) to determine if stimulation is having the appropriate psychological response, physiological measures from a stimulation subject (such as for example heart rate and other system measures) to determine if stimulation parameters are being applied safely, and/or other various safety markers.

These different methods can all be combined together in whole or in part and used to tune and/or alter the stimulation source characteristics, field parameters, calculated fields, the interface apparatus characteristics, and/or other qualities at any point before, during, or after stimulation to aid in the targeting (localizing) of stimulation, dosing of stimulation, characterizing safety parameters, and/or analyzing the online or offline effects of stimulation.

Furthermore, such imaging, biofeedback, physiological measurement, and other modalities in conjunction with the altered current generation could similarly be applied in the areas of altering cellular metabolism, physical therapy, drug delivery, and gene therapy as explained in the referenced patent application (U.S. patent application Ser. No. 11/764, 468, Apparatus and Method for Stimulation of Biological Tissue) and above as focused on treating OA. These examples are provided not to be exhaustive, but as an example of potential applications.

All of the methods, systems, and processes discussed in this document could be implemented with any form of stimulation, including but not limited to electromagnetic, acoustic, optical, thermal, electrical, magnetic, and/or combined methods (and/or methods which alter tissue impedances relative to electrical sources to generate altered stimulation currents, for example with electromagnetic, chemical, acoustic, optical, thermal, electrical, magnetic, and/or combined sources). Furthermore, all of the methods, systems, and processes could also be implemented before, during, and/or after stimulation.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

The invention may be embodied in other specific forms without departing from the spirit or essential characteristics thereof. The foregoing embodiments are therefore to be considered in all respects illustrative rather than limiting on the invention described herein.

What is claimed is:

1. A system for stimulating and monitoring tissue, the system comprising:
 a first non-invasive energy source that emits an electric field;
 a second non-invasive energy source that emits a mechanical field;
 an imaging device; and
 a controller comprising one or more programs that are configured to tune stimulation by identifying tissue distribution data of a subject from imaging data received from the imaging device, determining tissue boundaries in a stimulation area from the tissue distribution data, constructing a computational mesh that captures tissue segmentation demonstrated in the imaging data and accounts for tissue distribution and tissue boundaries, and calculating altered tissue mechanical properties in the stimulation area relative to the electrical field to be applied in the stimulation area, wherein the controller outputs a dose to be provided by the first and/or second non-invasive energy sources.

2. The system according to claim 1, wherein the imaging device is selected from the group consisting of: a magnetic resonance imaging device, a functional magnetic resonance imaging device, a device for performing a CT scan, and a device for performing electroencephalography.

3. The system according to claim 1, wherein the imaging device provides feedback to an operator as to the effect of the first and second energy sources on the tissue.

4. The system according to claim 1, wherein the second energy source is an ultrasound device.

5. The system according to claim 1, wherein the electric field is pulsed.

6. The system according to claim 1, wherein the electric field is time varying.

7. The system according to claim 1, wherein the electric field is pulsed a plurality of times, and each pulse may be for a different length of time.

8. The system according to claim 1, wherein the electric field is time invariant.

9. The system according to claim 1, wherein the mechanical field is pulsed.

10. The system according to claim 1, wherein the mechanical field is time varying.

11. The system according to claim 1, wherein the mechanical field is pulsed a plurality of times, and each pulse may be for a different length of time.

12. The system according to claim 1, wherein the electric field is focused.

13. The system according to claim 1, wherein the mechanical field is focused.

14. The system according to claim 1, wherein both the electric field and the mechanical field are focused.

15. The system according to claim 1, wherein the first and second energy sources are applied to a structure or multiple structures within the brain or the nervous system selected from the group consisting of: dorsal lateral prefrontal cortex, any component of the basal ganglia, nucleus accumbens, gastric nuclei, brainstem, thalamus, inferior colliculus, superior colliculus, periaqueductal gray, primary motor cortex, supplementary motor cortex, occipital lobe, Brodmann areas 1-48, primary sensory cortex, primary visual cortex, primary auditory cortex, amygdala, hippocampus, cochlea, cranial nerves, cerebellum, frontal lobe, occipital lobe, temporal lobe, parietal lobe, sub-cortical structures, and spinal cord.

16. The system according to claim 1, wherein the tissue is neural tissue.

17. The system according to claim 16, wherein the effect of the stimulation alters neural function past the duration of stimulation.

* * * * *